United States Patent
Bertoletti et al.

(10) Patent No.: US 11,576,932 B2
(45) Date of Patent: *Feb. 14, 2023

(54) NON-ACTIVATED T CELLS EXPRESSING EXOGENOUS VIRUS-SPECIFIC T CELL RECEPTOR (TCR)

(71) Applicant: Lion TCR Pte. Ltd., Singapore (SG)

(72) Inventors: Antonio Bertoletti, Singapore (SG); Sarene Koh, Singapore (SG)

(73) Assignee: Lion TCR Pte. Ltd.

( * ) Notice: Subject to any disclaimer, the term of this patent is extended or adjusted under 35 U.S.C. 154(b) by 1175 days.

This patent is subject to a terminal disclaimer.

(21) Appl. No.: 16/089,809

(22) PCT Filed: Mar. 31, 2016

(86) PCT No.: PCT/SG2016/050164
§ 371 (c)(1),
(2) Date: Sep. 28, 2018

(87) PCT Pub. No.: WO2017/171631
PCT Pub. Date: Oct. 5, 2017

(65) Prior Publication Data
US 2019/0192566 A1    Jun. 27, 2019

(51) Int. Cl.
*A61K 35/17*       (2015.01)
*C07K 14/70*       (2006.01)
*C12N 5/0783*      (2010.01)
*C07K 14/725*      (2006.01)
*A61P 31/20*       (2006.01)
*A61K 39/29*       (2006.01)
*C07K 14/02*       (2006.01)

(52) U.S. Cl.
CPC ............ *A61K 35/17* (2013.01); *A61K 39/292* (2013.01); *A61P 31/20* (2018.01); *C07K 14/02* (2013.01); *C07K 14/7051* (2013.01); *C12N 5/0638* (2013.01); *C12N 2510/00* (2013.01)

(58) Field of Classification Search
None
See application file for complete search history.

(56) References Cited

U.S. PATENT DOCUMENTS 11,186,624 B2 * 11/2021 Bertoletti ............ C12Q 1/6881

FOREIGN PATENT DOCUMENTS

| WO | 2007065957 A2 | 6/2007 |
| WO | 2009136874 A1 | 11/2009 |
| WO | 2014031687 A1 | 2/2014 |
| WO | 2015091823 A1 | 6/2015 |

OTHER PUBLICATIONS

Koh et al. (Molecular Therapy, 2013, p. 1-9 in IDS on Oct. 17, 2018).*

Ahlers JD, Belyakov IM. Memories that last forever: strategies for optimizing vaccine T-cell memory. Blood. Mar. 4, 2010;115(9):1678-89.

Alberti A, Caporaso N. HBV therapy: guidelines and open issues. Digestive and Liver Disease. Jan. 1, 2011;43:S57-63.

Chavez-Galan L, Arenas-Del Angel MC, Zenteno E, Chavez R, Lascurain R. Cell death mechanisms induced by cytotoxic lymphocytes. Cellular & molecular immunology. Feb. 2009;6(1):15.

Chattopadhyay PK, Betts MR, Price DA, Gostick E, Horton H, Roederer M, De Rosa SC. The cytolytic enzymes granyzme A, granzyme B, and perforin: expression patterns, cell distribution, and their relationship to cell maturity and bright CD57 expression. Journal of leukocyte biology. Jan. 1, 2009;85(1):88-97.

Cobbold M, Khan N, Pourgheysari B, Tauro S, McDonald D, Osman H, Assenmacher M, Billingham L, Steward C, Crawley C, Olavarria E. Adoptive transfer of cytomegalovirus-specific CTL to stem cell transplant patients after selection by HLA-peptide tetramers. Journal of Experimental Medicine. Aug. 1, 2005;202(3):379-86.

Flynn JK, Gorry PR. Stem memory T cells (TSCM)—their role in cancer and HIV immunotherapies. Clinical & translational immunology. Jul. 1, 2014;3(7):e20.

Fulcher DA, Wong SW. Carboxyfluorescein succinimidyl ester-based proliferative assays for assessment of T cell function in the diagnostic laboratory. Immunology and cell biology. Dec. 1999;77(6):559-64.

Gehring AJ, Xue SA, Ho ZZ, Teoh D, Ruedi C, Chia A, Koh S, Lim SG, Maini MK, Stauss H, Bertoletti A. Engineering virus-specific T cells that target HBV infected hepatocytes and hepatocellular carcinoma cell lines. Journal of hepatology. Jul. 1, 2011;55(1):103-10.

Gaudernack G, Leivestad T, Ugelstad J, Thorsby E. Isolation of pure functionally active CD8+ T cells positive selection with monoclonal antibodies directly conjugated to monosized magnetic microspheres. Journal of Immunological Methods. Jun. 24, 1986;90(2):179-87.

Hofmann C, Harrer T, Kubesch V, Maurer K, Metzner KJ, Eismann K, Bergmann S, Schmitt-Haendle M, Schuler G, Dörrie J, Schaft N. Generation of HIV-1-specific T cells by electroporation of T-cell receptor RNA. Aids. Aug. 20, 2008;22(13):1577-82.

Janeway et al., Immunobiology, (2001) 5th Edn, Garland Science, New York, Chapters 3, 6, 7 and 8.

(Continued)

*Primary Examiner* — Agnieszka Boesen
(74) *Attorney, Agent, or Firm* — Lerner, David, Littenberg, Krumholz & Mentlik, LLP

(57) ABSTRACT

The present invention relates to T cells, in particular a non-activated T cell, comprising an exogenous nucleic acid encoding a T cell Receptor (TCR) specific for a virus. An embodiment of the invention is directed to a non-activated (resting) T cell expressing Hepatitis B virus (HBV) envelope s183-191 TCR capable of inhibiting viral replication and which shows reduced expression of perforins and/or granzymes in response to stimulation as compared to an activated T cell expressing the said TCR. Also encompassed are methods for producing such cells, compositions, pharmaceutical compositions and kits comprising such cells and medical uses thereof.

19 Claims, 11 Drawing Sheets

Specification includes a Sequence Listing.

(56) References Cited

OTHER PUBLICATIONS

Jo J, Aichele U, Kersting N, Klein R, Aichele P, Bisse E, Sewell AK, Blum HE, Bartenschlager R, Lohmann V, Thimme R. Analysis of CD8+ T-cell-mediated inhibition of hepatitis C virus replication using a novel immunological model. Gastroenterology. Apr. 1, 2009;136(4):1391-401.

Koh S, Shimasaki N, Suwanarusk R, Ho ZZ, Chia A, Banu N, Howland SW, Ong AS, Gehring AJ, Stauss H, Renia L. A practical approach to immunotherapy of hepatocellular carcinoma using T cells redirected against hepatitis B virus. Molecular Therapy-Nucleic Acids. Jan. 1, 2013;2.

Liang TJ. Hepatitis B: the virus and disease. Hepatology. May 1, 2009;49(S5).

Lucifora J, Xia Y, Reisinger F, Zhang K, Stadler D, Cheng X, Sprinzl MF, Koppensteiner H, Makowska Z, Volz T, Remouchamps C. Specific and nonhepatotoxic degradation of nuclear hepatitis B virus cccDNA. Science. Mar. 14, 2014;343(6176):1221-8.

Haybaeck J, Zeller N, Wolf MJ, Weber A, Wagner U, Kurrer MO, Bremer J, lezzi G, Graf R, Clavien PA, Thimme R. A lymphotoxin-driven pathway to hepatocellular carcinoma. Cancer cell. Oct. 6, 2009;16(4):295-308.

Morgan RA, Chinnasamy N, Abate-Daga DD, Gros A, Robbins PF, Zheng Z, Feldman SA, Yang JC, Sherry RM, Phan GQ, Hughes MS. Cancer regression and neurologic toxicity following anti-MAGE-A3 TCR gene therapy. Journal of immunotherapy (Hagerstown, Md.: 1997). Feb. 2013;36(2):133.

Maus MV, Fraietta JA, Levine BL, Kalos M, Zhao Y, June CH. Adoptive immunotherapy for cancer or viruses. Annual review of immunology. Mar. 21, 2014;32:189-225.

Qasim W, Brunette M, Gehring AJ, Xue SA, Schurich A, Khakpoor A, Zhan H, Ciccorossi P, Gilmour K, Cavallone D, Moriconi F. Immunotherapy of HCC metastases with autologous T cell receptor redirected T cells, targeting HBsAg in a liver transplant patient. Journal of hepatology. Feb. 1, 2015;62(2):486-91.

Quabius ES, Krupp G. Synthetic mRNAs for manipulating cellular phenotypes: an overview. New biotechnology. Jan. 25, 2015;32(1):229-35.

Reinherz EL, Kung PC, Goldstein G, Schlossman SF. Separation of functional subsets of human T cells by a monoclonal antibody. Proceedings of the National Academy of Sciences. Aug. 1, 1979;76(8):4061-5.

Rooney CM, Smith CA, Ng CY, Loftin SK, Sixbey JW, Gan Y, Srivastava DK, Bowman LC, Krance RA, Brenner MK, Heslop HE. Infusion of cytotoxic T cells for the prevention and treatment of Epstein-Barr virus-induced lymphoma in allogeneic transplant recipients. Blood. Sep. 1, 1998;92(5):1549-55.

Storm P, Bartholdy C, Sorensen MR, Christensen JP, Thomsen AR. Perforin-deficient CD8+ T cells mediate fatal lymphocytic choriomeningitis despite impaired cytokine production Journal of virology Feb. 1, 2006;80(3):1222-30.

Scholten KB, Turksma AW, Ruizendaal JJ, van den Hende M, van der Burg SH, Heemskerk MH, Meijer CJ, Hooijberg E. Generating HPV specific T helper cells for the treatment of HPV induced malignancies using TCR gene transfer. Journal of translational medicine. Dec. 2011;9(1):147.

Lum LG, Orcutt-Thordarson N, Seigneuret MC, Hansen JA. In vitro regulation of immunoglobulin synthesis by T-cell subpopulations defined by a new human T-cell antigen (9.3). Cellular immunology Sep. 1, 1982;72(1): 122-9.

Thomas S, Klobuch S, Heemskerk M, Stolle D, Besold K, Plachter B, Voss H, Theobald M, Herr W. Giafting T-cells of CMV-seronegative donors with CMV-specific T-cell receptor RNA. InBONE Marrow Transplantation Mar. 1, 2010 (vol. 45, pp. S65-S66). Macmillan Building, 4 Crinan ST, London N1 9XW, England: Nature Publishing Group.

Thomas, S. et. al., Looking for most suitable cells forT-cell receptor RNA 1-40transfer—memory T cells offer considerable advantages Haematologica, Jun. 30, 2011, vol. 96, No. S2, pp. 212.

Wang B, Maile R, Greenwood R, Collins EJ, Frelinger JA. Naive CD8+ T cells do not require costimulation for proliferation and differentiation into cytotoxic effector cells. The Journal of Immunology. Feb. 1, 2000;164(3):1216-22.

Wilson JJ, Pack CD, Lin E, Frost EL, Albrecht JA, Hadley A, Hofstetter AR, Tevethia SS, Schell TD, Lukacher AE. CD8 T cells recruited early in mouse polyomavirus infection undergo exhaustion. The Journal of Immunology. Mar. 23, 2012:1103727.

Yoshimi A, Tsuge I, Namizaki H, Hoshino Y, Kimura H, Takahashi Y, Watanabe N, Kuzushima K, Kojima S. Epstein—Barr virus-specific T-cell cytotoxicity is mediated through the perforin pathway in patients with lymphoproliferative disorders after allogeneic bone marrow transplantation. British journal of haematology. Mar. 2002;116(3):710-5.

Zaritskaya L, Shurin MR, Sayers TJ, Malyguine AM. New flow cytometric assays for monitoring cell-mediated cytotoxicity. Expert review of vaccines. Jun. 1, 2010;9(6):601-16.

International Search Report for PCT/SG2016/050164 dated Jun. 24, 2016.

Cavalieri, S. et al.,"Human T lymphocytes transduced by lentiviral vectors in the absence of TCR activation maintain an intact immune competence," Blood, Jul. 15, 2003, pp. 497-505, vol. 102, No. 2, The American Society of Hematology. XP055455158.

Extended European Search Report including Written Opinion for Application No. 16897247.9 completed Oct. 10, 2019, 5 pages.

Perro, M. et al., "Generation of multi-functional antigen-specific human T-cells by lentiviral TCR gene transfer," Gene Therapy, Feb. 18, 2010, pp. 721-732, vol. 17, Macmillan Publishers. XP055296559.

\* cited by examiner

NON-ACTIVATED T CELLS EXPRESSING EXOGENOUS VIRUS-SPECIFIC T CELL RECEPTOR (TCR)

CROSS-REFERENCE TO RELATED APPLICATIONS

The present application is a national phase entry under 35 U.S.C. § 371 of International Application No. PCT/SG2016/050164 filed Mar. 31, 2016, published as International Publication No. WO 2017/171631 A1, incorporated herein by reference.

FIELD OF THE INVENTION

The present invention relates to T cells, in particular antiviral T cells, methods for producing such cells, compositions comprising such cells, and medical uses thereof.

BACKGROUND TO THE INVENTION

Current antiviral therapies are able to control HBV replication but cannot eliminate HBV cccDNA from infected hepatocytes. Standard therapeutic strategies are expensive, and either require life-long treatment, as is the case for treatment with nucleoside/nucleotide analogues, or are associated with severe negative side effects, as with IFN-α therapy. After several years of exposure to HBV antigens, HBV-specific T cells are often deleted or functionally exhausted in chronically-infected patients. Strategies to manipulate the virus-specific T cell response could lead to clinical therapies to treat chronic infections or prevent mortality related to severe acute infections.

Adoptive transfer of T lymphocytes engineered to achieve tumor specificity through the genetic insertion of either T cell receptors or chimeric antigen receptors (CARs) allows remarkable control of disseminated tumors. Engineering new HBV-specific T cell immunity through adoptive transfer of T cells expressing HBV-specific T cell receptors can reconstitute antiviral immunity that resembles one present in patients that resolve acute infection to control the virus, and represents a promising therapeutic strategy.

T cells engineered to express a hepatitis B virus (HBV)-specific TCR have been shown to be able to recognize natural hepatocellular carcinoma (HCC) cells expressing HBV antigens from integrated HBV DNA (Gehring et al., J Hepatol (2011) 55(1): 103-110), and activated T cells engineered by electroporation to express HBV-specific TCR have been shown to be capable of preventing HCC tumor cell seeding, and multiple infusions of such cells have been shown to control tumor growth in vivo (Koh et al., Mol Ther Nucleic Acids (2013) 2: e114). Moreover, adoptive T cell therapy with T cells expressing HBV surface Antigen (HBsAg)-specific TCR has been shown to suppress levels of HBsAg in a liver transplant patient with HCC metastases (Qasim et al., J Hepatol (2015) 62(2): 486-491).

However, there are serious side effects and/or toxicities associated with adoptive T cell therapy. Expression of low levels of target antigen in normal tissues, or cross-reactivity of the TCR with endogenous protein, can result in serious adverse effects. For example, Morgan et al., J Immunother (2013) 36(2): 133-151 describe neurological toxicity associated with adoptive T cell therapy with T cells engineered to express Anti-MAGE-A3 TCR, possibly as a result of expression of MAGE-A12 in human brain. Toxicity concerns have hindered implementation of therapy with adoptive transfer of virus-specific T cells directed against viruses infecting essential organs.

SUMMARY OF THE INVENTION

The present invention is based on the inventors' discovery that it is possible to engineer virus-specific T cells which are antiviral, and which do not exhibit substantial cytotoxicity to cells infected with the virus. An object of the present invention is to provide an intervention for the control of viral infection which displays reduced toxicity to the host.

In particular, the inventors have discovered that modifying non-activated T cells to express a TCR specific for a virus produces a T cell which is capable of inhibiting viral replication in cells infected with a virus, but which displays reduced cytotoxicity to those cells as compared to the cytotoxicity displayed by equivalent activated T cells engineered to express the TCR.

The inventors have also discovered that T cells comprising a TCR specific for a virus and which are modified for reduced expression/activity of cytotoxic factors retain ability to inhibit viral replication in cells infected with a virus, but display reduced cytotoxicity to those cells as compared to their non-modified counterparts.

In a first aspect, the present invention provides a T cell, optionally isolated, comprising exogenous nucleic acid encoding a T Cell Receptor (TCR) specific for a virus, wherein the T cell is a non-activated T cell. In some embodiments, the non-activated T cell does not display increased expression of perforin and/or granzyme in response to stimulation with peptide for which the TCR is specific. In some embodiments, the T cell is capable of inhibiting replication of the virus in a cell infected with the virus. In some embodiments, the T cell is capable of inhibiting replication of a virus in a cell infected with the virus to at least 50% of the inhibition of viral replication by an activated T cell comprising a TCR specific for the virus which is not modified for reduced expression or activity of a cytotoxic factor. In some embodiments, the T cell displays reduced cytotoxicity against cells infected with, or comprising a peptide of, the virus as compared to an activated T cell comprising a TCR specific for the virus which is not modified for reduced expression or activity of a cytotoxic factor.

In second aspect, the present invention provides a method, optionally an in vitro method, for producing a modified T cell specific for a virus, the method comprising modifying a T cell to express or comprise a T Cell Receptor (TCR) specific for the virus, wherein the modified T cell is a non-activated T cell. In some embodiments, the method is for producing a T cell according to the first aspect of the invention. In some embodiments, modifying the T cell to express or comprise a TCR specific for the virus comprises introducing nucleic acid encoding a TCR specific for the virus into the T cell. In some embodiments, the nucleic acid is introduced into the T cell by transduction, e.g. gammaretroviral transduction, lentiviral transduction. In some embodiments, the nucleic acid is introduced into the T cell by DNA or RNA transfection, e.g. mRNA electroporation. In some embodiments, the nucleic acid is introduced into the T cell by Transposon-based systems, e.g. Spleeping Beauty.

In a third aspect, the present invention provides a T cell is obtained or obtainable by the method according to the second aspect of the invention.

In fourth aspect, the present invention provides a pharmaceutical composition comprising a T cell according to the first or third aspects of the invention, and a pharmaceutically acceptable carrier, adjuvant, excipient, or diluent.

In a fifth aspect, the present invention provides a T cell according to the first or third aspects of the invention, or a pharmaceutical composition according to the fourth aspect of the invention, for use in a method of treating or preventing a disease or disorder.

In a sixth aspect, the present invention provides the use of a T cell according to the first or third aspects of the invention, or a pharmaceutical composition according to the fourth aspect of the invention in the manufacture of a medicament for use in a method of treating or preventing a disease or disorder.

In a seventh aspect, the present invention provides a method of treating or preventing a disease or disorder, comprising administering to a subject a therapeutically or prophylactically effective amount of a T cell according to the first or third aspects of the invention, or a pharmaceutical composition according to the fourth aspect of the invention.

In an eighth aspect, the present invention provides a method of treating or preventing a disease or disorder in a subject, comprising:
(a) isolating at least one T cell from a subject;
(b) modifying the at least one T cell to express or comprise a T Cell Receptor (TCR) specific for a virus; and
(c) administering the modified at least one T cell to the subject;
wherein the modified at least one T cell is a non-activated T cell. In some embodiments, modifying the at least one T cell to express or comprise a TCR specific for a virus comprises introducing nucleic acid encoding a TCR specific for a virus into the at least one T cell. In some embodiments, the nucleic acid is introduced into the T cell by transduction, e.g, gammaretroviral transduction, lentiviral transduction. In some embodiments, the nucleic acid is introduced into the at least one T cell by DNA or RNA transfection, e.g. mRNA electroporation. In some embodiments, the nucleic acid is introduced into the T cell by Transposon-based systems, e.g. Spleeping Beauty.

In a ninth aspect, the present invention provides a kit of parts comprising a predetermined quantity of the T cell according to the first or third aspects of the invention, or a pharmaceutical composition according to the fourth aspect of the invention.

In a tenth aspect, the present invention provides a T cell, optionally an isolated T cell, comprising a T Cell Receptor (TCR) specific for a virus, which is modified for reduced expression or activity of one or more cytotoxic factor. In some embodiments, the cytotoxic factor is selected from perforin, granzyme B, granzyme A, granulysin, and FASL. In some embodiments, the T cell is capable of inhibiting replication of the virus in a cell infected with the virus. In some embodiments, the T cell is capable of inhibiting replication of a virus in a cell infected with the virus to at least 50% of the inhibition of viral replication by an activated T cell comprising a TCR specific for the virus which is not modified for reduced expression or activity of a cytotoxic factor. In some embodiments, the T cell displays reduced cytotoxicity against cells infected with, or comprising a peptide of, the virus as compared to an activated T cell comprising a TCR specific for the virus which is not modified for reduced expression or activity of a cytotoxic factor. In some embodiments, the T cell comprises exogenous nucleic acid encoding the TCR.

In an eleventh aspect, the present invention provides a method, optionally an in vitro method, for producing a modified T cell specific for a virus, the method comprising modifying a T cell to reduce expression or activity of one or more cytotoxic factor, wherein the modified T cell comprises a T Cell Receptor (TCR) specific for the virus. In some embodiments the method is for producing a T cell according to the tenth aspect of the invention. In some embodiments, modifying a T cell to reduce expression or activity of one or more cytotoxic factor comprises treating the T cell with an agent for inhibiting expression or activity of one or more cytotoxic factor. In some embodiments the cytotoxic factor is selected from perforin, granzyme B, granzyme A, granulysin, and FASL. In some embodiments the method additionally comprises modifying the T cell to express or comprise a TCR specific for the virus. In some embodiments, modifying the T cell to express or comprise a TCR specific for the virus comprises introducing nucleic acid encoding a TCR specific for the virus into the T cell.

In a twelfth aspect, the present invention provides a T cell, optionally isolated, wherein the T cell is obtained or obtainable by the method according to the eleventh aspect of the invention.

In a thirteenth aspect, the present invention provides a pharmaceutical composition comprising a T cell according to the tenth or twelfth aspects of the invention, and a pharmaceutically acceptable carrier, adjuvant, excipient, or diluent.

In a fourteenth aspect, the present invention provides a T cell according to the tenth or twelfth aspects of the invention, or a pharmaceutical composition according to the thirteenth aspect of the invention, for use in a method of treating or preventing a disease or disorder.

In a fifteenth aspect, the present invention provides the use of a T cell according to the tenth or twelfth aspects of the invention, or a pharmaceutical composition according to the thirteenth aspect of the invention in the manufacture of a medicament for use in a method of treating or preventing a disease or disorder.

In a sixteenth aspect, the present invention provides a method of treating or preventing a disease or disorder, comprising administering to a subject a therapeutically or prophylactically effective amount of a T cell according to the tenth or twelfth aspects of the invention, or a pharmaceutical composition according to the thirteenth aspect of the invention.

In a seventeenth aspect, the present invention provides a method of treating or preventing a disease or disorder in a subject, comprising:
(a) isolating at least one T cell specific for a virus from a subject;
(b) modifying the at least one T cell for reduced expression or activity of one or more cytotoxic factor; and
(c) administering the modified at least one T cell to the subject.

In an eighteenth aspect, the present invention provides a method of treating or preventing a disease or disorder in a subject, comprising:
(a) isolating at least one T cell from a subject;
(b) modifying the at least one T cell to express or comprise a T Cell Receptor (TCR) specific for a virus, wherein:
  (i) the T cell is modified for reduced expression or activity of a cytotoxic factor, or
  (ii) the method further comprises modifying the at least one T cell for reduced expression or activity of one or more cytotoxic factor; and
(c) administering the modified at least one T cell to the subject. In some embodiments, modifying the at least one T cell to express or comprise a TCR specific for a virus comprises introducing nucleic acid encoding a TCR specific for a virus into the at least one T cell.

In some embodiments in accordance with the seventeenth and eighteenth aspects of the present invention, modifying the at least one T cell for reduced expression or activity of one or more cytotoxic factor comprises treating the at least one T cell with an agent for inhibiting expression or activity of one or more cytotoxic factor. In some embodiments, the cytotoxic factor is selected from perforin, granzyme B, granzyme A, granulysin, and FASL.

In a nineteenth aspect, the present invention provides a kit of parts comprising a predetermined quantity of a T cell according to the tenth or twelfth aspects of the invention, or a pharmaceutical composition according to the thirteenth aspect of the invention.

In a twentieth aspect, the present invention provides a kit of parts, comprising (i) a nucleic acid encoding a T Cell Receptor (TCR) specific for a virus and (ii) an agent for reducing the expression or activity of a cytotoxic factor.

In connection with various aspects, in some embodiments the present invention provides a T cell, optionally isolated, comprising a T Cell Receptor (TCR) specific for a virus, wherein the T cell (i) is capable of inhibiting replication of the virus in a cell infected with the virus, and (ii) displays reduced cytotoxicity against cells infected with, or comprising a peptide of, the virus as compared to an activated T cell comprising a TCR specific for the virus which is not modified for reduced expression or activity of a cytotoxic factor. In some embodiments, the T cell comprises exogenous nucleic acid encoding the TCR. In some embodiments the T cell exhibits a reduced level of expression or activity of one or more cytotoxic factors as compared to the level of expression or activity of an activated T cell which is not modified for reduced expression or activity of a cytotoxic factor. In some embodiments the T cell is modified for reduced expression or activity of one or more cytotoxic factor. In some embodiments the cytotoxic factor is selected from perforin, granzyme B, granzyme A, granulysin, and FASL. In some embodiments the T cell exhibits reduced expression or activity of one or more of RANTES, IL-13, MIP-1α and MIP-1β as compared to expression or activity of an activated T cell which is not modified for reduced expression or activity of a cytotoxic factor. In some embodiments the T cell is capable of inhibiting replication of a virus in a cell infected with the virus to at least 50% of the inhibition of viral replication by an activated T cell comprising a TCR specific for the virus which is not modified for reduced expression or activity of a cytotoxic factor.

In connection with various aspects, in some embodiments of the methods for producing a T cell specific for a virus according to the present invention, the method comprises modifying the T cell to express or comprise a TCR specific for the virus. In some embodiments, the modified T cell (i) is capable of inhibiting replication of the virus in a cell infected with the virus, and (ii) displays reduced cytotoxicity against cells infected with, or comprising a peptide of, the virus as compared to an activated T cell comprising a TCR specific for the virus which is not modified for reduced expression or activity of a cytotoxic factor. In some embodiments, modifying the T cell to express or comprise a TCR specific for the virus comprises introducing nucleic acid encoding a TCR specific for the virus into the T cell. In some embodiments, the nucleic acid is introduced into the T cell by transduction, e,g, gammaretroviral transduction, lentiviral transduction. In some embodiments, the nucleic acid is introduced into the T cell by DNA or RNA transfection, e.g. mRNA electroporation. In some embodiments, the nucleic acid is introduced into the T cell by Transposon-based systems, e.g. Spleeping Beauty. In some embodiments, modifying a T cell to reduce expression or activity of one or more cytotoxic factor comprises treating the T cell with an agent for inhibiting expression or activity of one or more cytotoxic factor. In some embodiments, the cytotoxic factor is selected from perforin, granzyme B, granzyme A, granulysin, and FASL.

DESCRIPTION

T Cells

In aspects according to the present invention, a T cell, optionally an isolated T cell, is provided. In accordance with the various aspects of the present invention herein, 'a T cell' may optionally be 'a population of T cells', and 'an isolated T cell' may optionally be 'an isolated population of T cells'.

CD8+ and CD4+ T cells are part of the adaptive immune system. The normal function of CD8+ T cells is to kill cancer cells and cells infected with intracellular pathogens, such as bacteria and viruses. CD4+ T cells are frequently characterised as T helper cells and facilitate the production of antibodies by B cells, enhance and maintain the responses of CD8+ T cells, and regulate macrophage activity.

T cells go through different stages of development, and have different phenotypes depending, for example, on whether the T cell has encountered antigen for which the T cell is specific, and the circumstances of any such encounter. T cell development and activation is described, for example, in Janeway et al., Immunobiology, (2001) 5th Edn, Garland Science, New York, Chapters 7 and 8, which are incorporated by reference in entirety.

An activated T cell is a T cell which has undergone the process of T cell activation. A T cell may become activated as a result of binding MHC-peptide complex for which the TCR of the T cell has high affinity in the context of a positive costimulatory signal from an antigen presenting cell (APC). Activation may be in vivo, ex vivo or in vitro. A T cell may also become activated as a result of stimulation through CD3, optionally in combination with stimulation through CD28, and optionally in combination with culture under high IL-2 conditions. In some embodiments an activated T cell may be activated in vitro or ex vivo, e.g. by stimulation through treatment with agonist anti-CD3 antibody, optionally in combination with treatment with agonist anti-CD28 antibody, and optionally in combination with culture under high IL-2 conditions. High IL-2 conditions may be an IL-2 concentration of >100 IU/ml, e.g. >500 IU/ml, >600 IU/ml, >800 IU/ml, >900 IU/ml.

A non-activated T cell is a T cell which has not been activated, i.e. has not undergone the process of T cell activation. Herein, a non-activated T cell may also be described as a resting T cell. In some embodiments a non-activated T cell is a T cell which has not encountered MHC-peptide complex for which the TCR of the T cell has high affinity in the context of a positive costimulatory signal from an APC. In some embodiments, a non-activated T cell is a T cell which has not been stimulated through CD3, optionally in combination with stimulation through CD28, and optionally in combination with culture under high IL-2 conditions. In some embodiments a non-activated T cell has not been activated in vitro or ex vivo, e.g. by stimulation through treatment with agonist anti-CD3 antibody, optionally in combination with treatment with agonist anti-CD28 antibody, and optionally in combination with culture under high IL-2 conditions.

In some embodiments according to various aspects of the present invention, an activated T cell may be a naïve T cell. In some embodiments according to various aspects of the present invention, a non-activated T cell may be a naïve T cell. As used herein, a naïve T cell is a T cell which has not encountered peptide or MHC-peptide complex for which the TCR of the T cell has high affinity, e.g. presented by an APC.

Non-activated and activated T cells can be characterized by reference to expression of certain markers, e.g. as described in Ahlers and Belyakov, Blood (2010) 115(9): 1678-1689, hereby incorporated by reference in its entirety. Non-activated and activated T cells may also be characterized in terms of functional properties of the cells.

In some embodiments, a non-activated T cell may express one or more of CD45RA, CCR7 or CD62L at the cell surface. In some embodiments a non-activated T cell may express higher levels of one or more of CD45RA, CCR7 or CD62L at the cell surface as compared to expression at the cell surface of an activated T cell.

In some embodiments, a non-activated T cell may have a $CD45RA^{high}$ phenotype. As used herein, a T cell having a $CD45RA^{high}$ phenotype is a cell which is determined e.g. by flow cytometry to express high levels of CD45RA at the cell surface. The skilled person is readily able to determine a cell or population of cells displaying 'high' surface expression of a given molecule, e.g. by analysis by flow cytometry, for example by reference to a control cell or population of cells which does not express that molecule at the cell surface, or which expresses the molecule at a lower level of expression.

In some embodiments a non-activated T cell may express a lower level of one or more of CD45RO, CD43 or KLRG1 at the cell surface as compared to expression at the cell surface of an activated T cell, or may not express one or more of CD45RO, CD43 or KLRG1 at the cell surface at a detectable level.

It is known that non-activated (resting) T cells display little of no expression of cytolytic enzymes and lower expression of certain cytokines as compared with more differentiated cell types (Chattopadhyay et al., J Leukoc Biol (2009) 85(1): 88-97, hereby incorporated by reference in its entirety).

Accordingly, in some embodiments, a non-activated T cell may be defined by a lower level of expression by one or more of perforin, granzyme (e.g. granzyme B or granzyme A), or granulysin as compared to expression by an activated T cell. In some embodiments, a non-activated T cell may not express one or more of perforin, granzyme (e.g. granzyme B or granzyme A), or granulysin at a detectable level. In some embodiments, a non-activated T cell may express a lower level of one or more of perforin, granzyme (e.g. granzyme B or granzyme A), or granulysin following stimulation with a peptide for which the non-activated T cell comprises a specific TCR as compared to expression by an activated T cell following stimulation with a peptide for which the activated T cell comprises a specific TCR.

In some embodiments, a non-activated T cell may not express one or more of perforin, granzyme (e.g. granzyme B or granzyme A), or granulysin at a detectable level following stimulation with a peptide for which the non-activated T cell comprises a specific TCR (e.g. as determined by flow cytometry). In some embodiments, expression of one or more of perforin, granzyme (e.g. granzyme B or granzyme A), or granulysin by a non-activated T cell following stimulation with a peptide for which the non-activated T cell comprises a specific TCR is not increased as compared to expression by a non-activated T cell which has not been stimulated with a peptide for which the non-activated T cell comprises a specific TCR.

Stimulation with peptide may be performed as described herein in Example 6. Briefly, cells expressing MHC capable of presenting the peptide for which the T cell comprises a specific TCR may be pulsed with 1 μg/ml of the peptide for 1 h, washed twice and then co-cultured for 5 h or overnight with the T cells, optionally in the presence of brefeldin A.

Gene/protein expression of perforin, granzyme (e.g. granzyme B or granzyme A), or granulysin can be analysed and quantified as described herein. In some embodiments, following stimulation with a peptide for which the non-activated T cell comprises a specific TCR, the non-activated T cell according to the present invention may express of one or more of perforin, granzyme (e.g. granzyme B or granzyme A), or granulysin at a level which is less than 2 times, less than 1.9 times, less than 1.8 times, less than 1.7 times, less than 1.6 times, less than 1.5 times, less than 1.4 times, less than 1.3 times, less than 1.2 times, or less than 1.1 times the level of expression by the non-activated T cell before stimulation with peptide, or the level of expression by a control non-activated T cell which is not stimulated with peptide.

In embodiments herein, stimulation of a T cell with a peptide includes contacting a T cell with the peptide, a virus comprising the peptide, a cell comprising the peptide, or a cell comprising (e.g. infected with) a virus comprising the peptide. In some embodiments a cell comprising the peptide may have been modified to comprise or express the peptide. For example, in some embodiments the cell may have been modified to comprise nucleic acid encoding the peptide, or may have been pulsed with the peptide. In some embodiments stimulation may be in vitro. In some embodiments stimulation may be ex vivo.

In some embodiments, a non-activated T cell may express a lower level of one or more of RANTES, IL-13, MIP-1α and MIP-1β as compared to expression by an activated T cell. Expression may be gene or protein expression, as explained herein below.

In some embodiments, an activated T cell may express one or more of CD45RO, CD43 or KLRG1 at the cell surface. In some embodiments an activated T cell may express higher levels of one or more of CD45RO, CD43 or KLRG1 at the cell surface as compared to expression at the cell surface of a non-activated T cell. In some embodiments an activated T cell may express a lower level of one or more of CD45RA, CCR7 or CD62L at the cell surface as compared to expression at the cell surface of a non-activated T cell, or may not express one or more of CD45RA, CCR7 or CD62L at the cell surface at a detectable level. In some embodiments, an activated T cell may have a $CD45RA^{low}$ phenotype. As used herein, a T cell having a $CD45RA^{low}$ phenotype is a cell which is determined e.g. by flow cytometry to express CD45RA at the cell surface at a detectable level, but which expresses CD45RA at the cell surface at a level which is not a high level of expression. The skilled person is readily able to determine a cell or population of cells displaying 'low' surface expression of a given molecule, e.g. by analysis by flow cytometry, for example by reference to a control cell or population of cells which expresses that molecule at the cell surface at a higher level of expression.

In some embodiments, an activated T cell may express a higher level of one or more of perforin, granzyme (e.g. granzyme B or granzyme A), or granulysin as compared to expression by a non-activated T cell. In some embodiments, an activated T cell may express a higher level of one or more of perforin, granzyme (e.g. granzyme B or granzyme A), or granulysin following stimulation with a peptide for which the activated T cell comprises a specific TCR as compared to expression by a non-activated T cell following stimulation with a peptide for which the non-activated T cell comprises a specific TCR.

In some embodiments, an activated T cell may express a higher level of one or more of RANTES, IL-13, MIP-1α and MIP-1β as compared to expression by a non-activated T cell.

In some embodiments, a non-activated T cell may display reduced cytotoxic activity against a cell infected with, or comprising a peptide of, the virus for which the non-activated T cell is specific as compared to the cytotoxicity displayed by an activated T cell against a cell infected with, or comprising a peptide of, the virus for which the activated T cell is specific. In some embodiments, a non-activated T cell may not display cytotoxic activity against a cell infected with, or comprising a peptide of, the virus for which the non-activated T cell is specific.

In some embodiments, a non-activated T cell may have a lower rate of cell division (i.e. the cell may undergo fewer cell divisions per unit time) as compared to the rate of cell division of an activated T cell. The rate of cell division for a given cell/population can be analysed, for example, by in vitro analysis of incorporation of $^3$H-thymidine or CFSE dilution assay, e.g. as described in Fulcher and Wong, Immunol Cell Biol (1999) 77(6): 559-564, hereby incorporated by reference in entirety.

As used herein, 'cytotoxicity' refers to cell death, or induction of cell death, of a cell infected with, or comprising a peptide of, a virus for which the T cell is specific and/or presenting a peptide of the virus. Cytotoxic activity of a given T cell or population of T cells can be measured by suitable means well known to the skilled person, for example by measuring levels of markers of cell lysis following contacting the T cell or population of T cells with cells infected with, or comprising a peptide of, the virus. In some embodiments, the cytotoxicity is in relation to a cell infected with, or comprising a peptide of, a virus, as described herein.

In particular embodiments, non-activated T cells and activated T cells may be distinguished by reference to one or more of the following features:

a) non-activated T cells having a CD45RA$^{high}$, CD62L$^{high}$ phenotype;
b) activated T cells having a CD45RA$^{low}$, CD62L$^{high}$ phenotype;
c) non-activated T cells not displaying increased expression (e.g. gene or protein expression) of perforin and/or granzyme in response to stimulation with peptide for which the T cell comprises a specific TCR;
d) activated T cells displaying increased expression (e.g. gene or protein expression) of perforin and/or granzyme in response to stimulation with peptide for which the T cell comprises a specific TCR;
e) a higher level of expression of CD45RA at the cell surface of non-activated T cells as compared to expression at the cell surface of activated T cells, e.g. as determined by flow cytometry;
f) a lower level of expression of perforin and/or granzyme by non-activated T cells following stimulation with a peptide for which the non-activated T cell comprises a specific TCR as compared to expression by activated T cells following stimulation with a peptide for which the activated T cell comprises a specific TCR, e.g. as determined by gene or protein expression;

g) a lower level of expression of one or more of RANTES, IL-13, MIP-1α and MIP-1β by non-activated T cells as compared to expression by activated T cells, e.g. as determined by gene or protein expression (e.g. by ELISA);
h) a lower rate of cell division for non-activated T cells as compared to the rate of cell division for activated T cells;
i) a lower level of cytotoxicity against cells infected with, or comprising a peptide of, a virus for which the T cell comprises a specific TCR for non-activated T cells as compared to activated T cells, e.g. as determined in an in vitro assay for cytotoxicity.

In accordance with the present disclosure, non-activated and/or activated T cells may be characterized before or after modification, e.g. to express or comprise a TCR specific for a virus.

In some embodiments, the activated and non-activated T cells for the purposes of such comparisons may be the same except for their non-activated/activated state, e.g. as described herein. In some embodiments the non-activated T cell and the activated T cell comprise or express the same TCR. In some embodiments the activated T cell is derived from a non-activated T cell by activation, e.g. in vitro.

Expression of markers by T cells can be determined by various methods well known to the skilled person. As used herein, 'expression' may refer to gene expression or protein expression. Gene expression can be measured by various means well known to those skilled in the art. For example, expression of a given gene can be measured by measuring levels of mRNA, for example by quantitative real-time PCR (qRT-PCR), or by reporter-based methods. Similarly, protein expression can be measured by various methods well known in the art, e.g. antibody-based methods, for example by western blot, immunohistochemistry, immunocytochemistry, flow cytometry, ELISA, etc. Expression can also be measured by reporter-based methods.

For example, expression of cell surface markers can be analysed by contacting cells with an agent (e.g. an antibody) capable binding specifically to the marker of interest, and by detecting binding of the agent to the cells, e.g. by analysis by flow cytometry. Activities of cells can be analysed e.g. using an in vitro assay for the activity of interest.

In accordance with the present disclosure, readouts for expression or activities may be compared between cells or samples, or may compared to reference values. For example, levels may be compared between non-activated T cells and activated T cells. In some embodiments, the level of expression/activity is calculated for an individual cell, or for a population of cells. In some embodiments the level of expression/activity is an average for a cell or population of cells, e.g. the mean or median level of expression/activity.

In some embodiments, a cell having reduced/lower level of expression of a given gene or protein, or having reduced/lower level of a given activity, relative to another cell may have a level of expression/activity which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the level of expression/activity by the reference cell.

In some embodiments, a cell having increased/higher level of expression of a given gene or protein, or having increased/higher level of a given activity, relative to another cell, has one of more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the level of the level of expression/activity by the reference cell.

In addition to the above phenotypic markers, T cells may be distinguished from other cells (e.g. other lymphocytes and/or leukocytes) based on detection of one or more markers for T cells. T cell markers include CD3 polypeptides (e.g. CD3γ CD3ε CD3ζ or CD3δ), TCR polypeptides (TCRα or TCRβ), CD27, CD28, CD4 and CD8.

Virus Specificity

The present invention is particularly concerned with virus specific T cells, i.e. T cells reactive to cells infected with, or comprising a peptide of, a virus.

A virus specific T cell according to the present invention comprises a TCR capable of binding to an MHC molecule presenting a peptide derived from the virus for which the T cell is specific.

T Cell Receptors (TCRs) are heterodimeric, antigen-binding molecules typically comprising an α-chain and a β-chain. In nature, α-chain and a β-chains are expressed at the cell surface of T cells (αβ/T cells) as a complex with invariant CD3 chains. An alternative TCR comprising γ and δ chains is expressed on a subset of T cells (γδ T cells). TCRs recognise (bind to) antigen peptide presented by major histocompatibility complex (MHC) molecules. TCR structure and recognition of the peptide-MHC complex is described in detail for example in Immunobiology, 5$^{th}$ Edn. Janeway C A Jr, Travers P, Walport M, et al. New York: Garland Science (2001), Chapters 3 and 6, which are hereby incorporated by reference in their entirety.

A peptide derived from a virus may be derived from a virion or encoded by nucleic acid from a virus. As used herein a "peptide" refers to a chain of two or more amino acid monomers linked by peptide bonds. In some embodiments a peptide may be 50 amino acids or fewer in length. In some embodiments, the peptide is one of 5-15, 5-14, 5-13, 5-12, 5-11, 5-10, 5-9 or 5-8 amino acids in length. In some embodiments, the peptide is one of 5-15, 6-15, 7-15, 8-15, 9-15, 10-15, 11-15 or 12-15 amino acids in length. In some embodiments, the peptide is one of 5, 6, 7, 8, 9, 10, 11, 12, 13, 14, or 15 amino acids in length.

The peptide is presented by an MHC molecule, e.g. an MHC class I molecule. MHC class I molecules are heterodimers of an α-chain and a β2-microglobulin. The α-chain has three domains designated α1, α2 and α3. The α1 and α2 domains together form the groove to which the peptide presented by the MHC class I molecule binds, to form the peptide-MHC complex. MHC class I α-chains are polymorphic, and different α-chains are capable of binding and presenting different peptides. In humans MHC class I α-chains are encoded by human leukocyte antigen (HLA) genes.

The TCR of the T cell according to the present disclosure is capable of binding to a peptide derived from a virus polypeptide presented by an MHC class I molecule.

The virus according to the present invention is not limited, and may be any virus. A virus may be a dsDNA virus (e.g. adenovirus, herpesvirus, poxvirus), ssRNA virus (e.g. parvovirus), dsRNA virus (e.g. reovirus), (+)ssRNA virus (e.g. picornavirus, togavirus), (−)ssRNA virus (e.g. orthomyxovirus, rhabdovirus), ssRNA-RT virus (e.g. retrovirus) or dsDNA-RT virus (e.g. hepadnavirus).

In particular, the present disclosure contemplates viruses of the families adenoviridae, herpesviridae, papillomaviridae, polyomaviridae, poxviridae, hepadnaviridae, parvoviridae, astroviridae, caliciviridae, picornaviridae, coronaviridae, flaviviridae, togaviridae, hepeviridae, retroviridae, orthomyxoviridae, arenaviridae, bunyaviridae, filoviridae, paramyxoviridae, rhabdoviridae and reoviridae.

Viruses associated with a disease or disorder are of particular interest. Accordingly, the following viruses are contemplated in connection with the present invention: adenovirus, Herpes simplex type 1 virus, Herpes simplex type 2 virus, Varicella-zoster virus, Epstein-barr virus, Human cytomegalovirus, Human herpesvirus type 8, Human papillomavirus, BK virus, JC virus, Smallpox, Hepatitis B virus, Parvovirus B19, Human Astrovirus, Norwalk virus, coxsackievirus, hepatitis A virus, poliovirus, rhinovirus, severe acute respiratory syndrome virus, hepatitis C virus, yellow fever virus, dengue virus, West Nile virus, TBE virus, Rubella virus, Hepatitis E virus, Human immunodeficiency virus, influenza virus, lassa virus, Crimean-Congo hemorrhagic fever virus, Hantaan virus, ebola virus, Marburg virus, measles virus, mumps virus, parainfluenza virus, respiratory syncytial virus, rabies virus, hepatitis D virus, rotavirus, orbivirus, coltivirus, and banna virus.

In particular embodiments the virus may be a hepatitis virus, e.g. hepatitis B virus.

In some embodiments, the virus may be a virus which is not directly cytopathic to cells infected with the virus.

The cell to which the T cell according to the invention is reactive may be a cell infected with the virus, or may be a cell comprising or expressing a peptide of the virus. The cell infected with or comprising or expressing the virus may present a peptide of the virus in the context of an MHC class I molecule at the cell surface.

The cell infected with, or comprising a peptide of, a virus may comprise an HLA allele encoding a MHC class I molecule capable of presenting the peptide of the virus for which a TCR of the T cell is specific. In some embodiments the cell infected with, or comprising a peptide of, a virus may be HLA matched for the viral peptide recognised by a TCR of the T cell. In some embodiments the T cell is obtained from a donor who is HLA matched for the viral peptide recognised by a TCR of the T cell.

In some embodiments the cell may express or comprise a peptide of the virus as a result of being infected with the virus. In some embodiments the cell may have been modified to comprise or express a peptide of the virus. For example, in some embodiments the cell may have been modified to comprise nucleic acid encoding a peptide of the virus, or may have been pulsed with a peptide of the virus.

In particular embodiments, the T cell according to the present invention may comprise a TCR capable of recognizing a peptide of a polypeptide encoded by the nucleic acid region of HBV encoding the virus envelope proteins, known as "env". Herein a HBV polypeptide encoded by the env region is referred to as an "Env polypeptide". In some embodiments, the peptide recognised by a TCR or T cell according to the present invention comprises a sequence of amino acids comprising amino acids at positions 171-180 of HBV Env polypeptide, wherein the residues of Env are numbered relative to Env from HBV genotype B. In some embodiments, the peptide comprises, or consists of, the sequence of amino acids comprising positions 171-180 of HBV Env polypeptide, FLGPLLVLQA (SEQ ID NO:1) or LLGPLLVLQA (SEQ ID NO:2), or variant thereof having one or two or three amino acid substitutions in the amino acid sequence. In some embodiments, the peptide additionally comprises 1, 2, 3, 4, 5 amino acids at one or both ends of the amino acid sequence. In some embodiments, the peptide additionally comprises 1-2, 1-3, 1-4, or 1-5 amino acids at one or both ends of the amino acid sequence.

Antiviral Activity

The T cell according to the present invention is an antiviral T cell. As used herein, an antiviral T cell possesses antiviral activity against a virus.

Antiviral activity as used herein refers to inhibition of viral replication or function. In particular, antiviral activity may reduce or inhibit one or more of: attachment to a cell by a virus, entry of a cell by a virus, release of viral protein and/or viral nucleic acid into a cell, replication of a virus within a cell, assembly of viral particles, or release of viral particles from a cell for the infection of further cells. In some embodiments the T cell according to the present invention is capable of inhibiting/reducing replication of the virus in an infected cell.

In some embodiments, antiviral activity refers to non-cytotoxic (e.g. non-cytolytic) inhibition of viral replication or function; that is, inhibition of viral replication or function which does not cause cell death (e.g. cell lysis) of the infected cell.

As used herein, viral replication refers to the formation of viral particles in a cell infected with a virus. Inhibition of viral replication by a particular treatment can be determined by methods known to the person skilled in the art, such as by detection of a reduced amount of virus in a cell infected with the virus following a particular treatment as compared to the amount of virus in the absence of such the treatment, or following a control treatment.

In accordance with the present disclosure, ability of a T cell to inhibit viral replication can be determined by detection of a reduced amount of virus in a cell infected with a virus following culture in the presence of the T cell as compared to the amount of virus in a cell infected with the virus following culture in the absence of exposure to a T cell according to the invention. Ability of a virus specific T cell to inhibit viral replication can be determined by detection of a reduced amount of virus in a cell infected with a virus following culture in the presence of the virus specific T cell as compared to the amount of virus in a cell infected with the virus following culture in the absence of exposure to a T cell according to the invention, or following culture in the presence of a T cell which is not specific for the virus.

Inhibition of viral replication may be determined in a cell infected with the virus or a plurality thereof, a sample comprising one or more cells infected with the virus, or a sample obtained from a subject infected with the virus.

The amount of virus in a given cell, population of cells or sample can be quantified by methods well known to the skilled person, such as those reviewed in Albertoni et al., Int J Infec Dis (2014) 25: 145-149, hereby incorporated by reference in its entirety. The amount of virus may be calculated as the viral load. Methods include analysis by quantitative PCR and/or RT-PCR for viral nucleic acid, plaque assays, focus-forming assays, endpoint dilution assays, and methods for detection and quantification of viral polypeptides/peptides or activity, such antibody-based methods (e.g. western blot, immunohistochemistry, immunocytochemistry, flow cytometry, ELISA, ELISPOT), or reporter-based methods.

In some embodiments, a T cell according to the present invention displays antiviral activity (e.g. inhibition of viral replication) which is at least 10%, 20%, 50%, 55% 60%, 65%, 70%, 75%, 80%, 85%, 90%, 95%, 96%, 97%, 98%, 99% or 100% of the antiviral activity displayed by a reference cell, e.g. an activated T cell comprising a TCR specific for the virus.

In some embodiments, antiviral activity of a T cell according to the present invention is analysed in relation to a cell infected with, or comprising a peptide of, a virus for which the T cell is specific as compared to a reference cell, e.g. an activated T cell comprising a TCR specific for the virus. In some embodiments, the reference cell is an activated T cell which comprises a TCR which is the same as a TCR of the T cell according to the invention. In some embodiments, the reference cell is the same as the T cell according to the invention except that the reference T cell has an activated phenotype, e.g. as described herein. In some embodiments, the antiviral activity is analysed in relation to a cell infected with, or comprising a peptide of, a virus, as described herein.

In particular embodiments, a T cell according to the invention is capable of inhibiting replication of a virus in a cell infected with the virus to at least 10%, 20%, 50%, 55% 60%, 65%, 70%, 75%, 80%, 85%, 90%, 95%, 96%, 97%, 98%, 99% or 100% of the inhibition of viral replication by an activated T cell comprising a TCR specific for the virus which is not modified for reduced expression or activity of a cytotoxic factor. In some embodiments, the relative inhibition is at least 50%. In some embodiments the relative inhibition is one of 55% 60%, 65%, 70%, 75%, 80%, 85%, 90%, 95%, 96%, 97%, 98%, 99% or 100%.

It is a particularly surprising finding that a T cell comprising a TCR specific for a virus which displays reduced cytotoxicity against cells infected with, or comprising a peptide of, the virus as compared to an activated T cell comprising a TCR specific for the virus retains considerable antiviral activity.

In some embodiments, the antiviral activity may be LTβR-dependent. In some embodiments, the antiviral activity may involve signaling through LTβR. In some embodiments, the antiviral activity may involve interaction between LTβR and LIGHT, or interaction between LTβR and LTβ. In some embodiments, the antiviral activity may involve LTβR/LIGHT signaling, or LTβR/LTβ signaling. In some embodiments, the antiviral activity may involve degradation of viral DNA.

The mechanism of antiviral activity displayed by a T cell can be investigated, for example, as described in the Examples of the present application.

Cytotoxicity

The T cell according to the present invention displays reduced cytotoxicity as compared to a reference cell.

As used herein, cytotoxicity refers to the capacity of a T cell to effect cell death in another cell, e.g. a cell comprising or expressing a viral peptide or nucleic acid, e.g. as a result of viral infection.

T cells are capable of effecting cell death in cells infected with a virus by releasing cytotoxic factors including perforin, granzyme (e.g. granzyme B or granzyme A), granulysin, and/or by inducing apoptosis of the infected cell by ligating FAS on the infected cell through FASL expressed on the T cell (described for example by Chavez-Galan et al., Cellular and Molecular Immunology (2009) 6(1): 15-25, hereby incorporated by reference in its entirety).

Cytotoxicity of a T cell to a given target cell (i.e. a cell infected with HBV or comprising or expressing an HBV peptide) can be investigated, for example, using any of the methods reviewed in Zaritskaya et al., Expert Rev Vaccines (2011), 9(6):601-616, hereby incorporated by reference in its entirety. One example of an assay for cytotoxicity of a T cell for to a target cell is the $^{51}$Cr release assay, in which target cells are treated with $^{51}$Cr, which they internalise. Lysis of the target cells by T cells results in the release of the radioactive $^{51}$Cr into the cell culture supernatant, which can be detected.

Other methods may include detection of markers of cell damage. For example, aspartate transaminase (AST) levels may be detected as a measure of damage of e.g. liver cells. In accordance with the present invention, cytotoxicity of a given T cell against a liver cell infected with a virus can be determined by incubating an infected cell with a T cell in vitro, and subsequently detecting the level of AST. Cytotoxicity can also be analysed by imaging of cells, e.g. by static or live imaging as described in the Examples herein.

In some embodiments, a T cell according to the present invention displays reduced cytotoxicity against a cell infected with, or comprising a peptide of, a virus for which the T cell is specific as compared to a reference cell, e.g. an activated T cell comprising a TCR specific for the virus. In some embodiments, the reference cell is an activated T cell which comprises a TCR which is the same as a TCR of the T cell according to the invention. In some embodiments, the reference cell is the same as the T cell according to the invention except that the reference T cell has an activated phenotype, e.g. as described herein. In some embodiments, the cytotoxicity is analysed in relation to a cell infected with, or comprising a peptide of, a virus, as described herein. It will be appreciated that the reference activated T cell has not been modified for reduced expression of one or more cytotoxic factors.

In some embodiments, a T cell according to the present invention displays cytotoxicity which is less than 100%, 95%, 90%, 85%, 80%, 75%, 70%, 65%, 60%, 55%, 50%, 45%, 40%, 35%, 30%, 25%, 20%, 15%, 10%, 5%, 2%, or 1% of the cytotoxicity displayed by a reference cell in a comparable assay.

In particular, it is an object of the present invention to provide a T cell comprising a TCR specific for a virus which (i) displays antiviral activity (e.g. inhibition of viral replication) which is at least 10%, 20%, 50%, 55% 60%, 65%, 70%, 75%, 80%, 85%, 90%, 95%, 96%, 97%, 98%, 99% or 100% of the antiviral activity displayed by an activated T cell comprising the same TCR specific for the virus, and (ii) displays cytotoxicity against a cell infected with the virus which is less than 100%, 95%, 90%, 85%, 80%, 75%, 70%, 65%, 60%, 55%, 50%, 45%, 40%, 35%, 30%, 25%, 20%, 15%, 10%, 5%, 2%, or 1% of the cytotoxicity displayed by an activated T cell comprising the same TCR specific for the virus, in a comparable assay.

Engineered T Cells

In various aspects, the present invention provides non-naturally occurring products. Such products may be variously referred to as recombinant, artificial, non-native or man-made products. In particular, the present invention relates to exogenous TCRs, nucleic acids and T cells.

"Exogenous" as used herein generally means not endogenous. In the context of a cell, an exogenous TCR may refer to a TCR which is not encoded by nucleic acid of that cell, e.g. prior to any introduction of nucleic acid encoding the exogenous TCR into the cell. An exogenous nucleic acid refers to a nucleic acid not present in that cell e.g. prior to any introduction of the nucleic acid into the cell.

In the context of a subject, an exogenous TCR may refer to a TCR which is not present in the subject or encoded by nucleic acid, e.g. of the genome, of the subject, prior to any introduction of the TCR into the subject. An exogenous nucleic acid refers to a nucleic acid not present in that subject, e.g. prior to any introduction of the nucleic acid into the subject. An exogenous cell refers to a cell not present in that subject, e.g. prior to any introduction of a cell and/or nucleic acid into the subject.

In connection with various aspects, the present invention includes nucleic acid encoding a TCR. In some embodiments, the nucleic acid is purified or isolated, e.g. from other nucleic acid, or naturally-occurring biological material. In some embodiments, the nucleic acid comprises (a) a nucleic acid sequence encoding a TCR α-chain comprising a variable region and a constant region. In some embodiments, the nucleic acid comprises (b) a nucleic acid sequence encoding a TCR β-chain comprising a variable region and a constant region. In some embodiments, the nucleic acid comprises (a) a nucleic acid sequence encoding a TCR α-chain comprising a variable region and a constant region, and (b) a nucleic acid sequence encoding a TCR β-chain comprising a variable region and a constant region.

It may be desirable to express TCR α- and β-chains as a fusion protein. This may for example be desirable to achieve similar levels of protein expression for each chain. Accordingly, in some embodiments, the nucleic acid additionally comprises (c) a nucleic acid sequence encoding a linker sequence. A "linker sequence" as used herein refers to a sequence of amino acids for linking expressed peptide or polypeptide sequences. In the present invention, a linker sequence is for linking TCR α- and β-chains.

In some embodiments, it may be desirable to separate TCR α- and β-chains expressed as a fusion protein. In some embodiments, this may be achieved by providing for cleaving the fusion protein between the TCR α- and β-chains.

Accordingly, in some embodiments, the linker sequence may be a cleavable linker. That is, the linker sequence may comprise a sequence of amino acids which is capable of being cleaved. For example, the linker sequence may comprise a sequence capable of acting as a substrate for an enzyme capable of cleaving peptide bonds—i.e. a cleavage site. Many such cleavage sites are known to and can be employed by the person skilled in the art of molecular biology. In some embodiments, the cleavable linker may comprise an autocleavage site. Autocleavage sites are automatically cleaved without the need for treatment with enzymes. An example of an autocleavage site is the 2A sequence from Picornavirus "NPGP", which is cleaved at "G/P". This autocleavage sequence is herein referred to as "Picornavirus 2A (P2A)". A linker sequence comprising P2A is herein referred to as a P2A linker.

In it will be appreciated that where it is desired for TCR α- and β-chains to be expressed as a single polypeptide joined by a linker sequence, the nucleic acid sequences encoding the TCR α- and β-chains and linker must be provided in the same reading frame.

Nucleic acids used in connection with the present invention may comprise sequences (a) and (b), and optionally (c), in particular orientations in the nucleic acid. That is, the sequences may be provided in a particular order. The particular 5' to 3' order of sequences (a) and (b), and optionally (c) may influence e.g. transcription, post-transcriptional processing, translation, post-translational processing, folding, associations, stability, degradation, trafficking, and/or functional properties of the nucleic acid/expressed product.

In some embodiments of the nucleic acid according to the invention sequences (a) and (b) are provided in the 5' to 3' orientation: 5'-(b)-(a)-3'. In some embodiments, sequences (a) and (b) are provided in the 5' to 3' orientation: 5'-(a)-(b)-3'. In some embodiments, sequences (a), (b) and (c) are provided with the 5' to 3' orientation: 5'-(b)-(c)-(a)-3'. In some embodiments, sequences (a), (b) and (c) are provided with the 5' to 3' orientation: 5'-(a)-(c)-(b)-3'.

In some embodiments, the nucleic acids encode one or more structural features for increasing and/or stabilising association between expressed TCR α- and β-chains. In some embodiments, the feature may be a particular amino acid or sequence of amino acids. In some embodiments, the nucleic acid may encode one or more non-native cysteine residues for forming one or more disulphide bonds between the TCR α- and β-chains. In some embodiments, the nucleic acid may encode one or more non-native cysteine residues in the constant region of the TCR α- and/or β-chains.

Embodiments of aspects of the present invention include the use of a vector comprising a nucleic acid as described herein.

A "vector" as used herein is a nucleic acid (DNA or RNA) used as a vehicle to transfer exogenous nucleic acid into a cell. The vector may be an expression vector for expression of the nucleic acid in the cell. Such vectors may include a promoter sequence operably linked to the nucleic acid encoding the sequence to be expressed. A vector may also include a termination codon and expression enhancers. Any suitable vectors, promoters, enhancers and termination codons known in the art may be used to express polypeptides from a vector according to the present disclosure. Suitable vectors include plasmids, binary vectors, DNA vectors, mRNA vectors, viral vectors (e.g. gammaretroviral vectors, lentiviral vectors, adenovirus vectors), transposon-based vectors, and artificial chromosomes (e.g. yeast artificial chromosomes), e.g. as described in Maus et al., Annu Rev Immunol (2014) 32:189-225, which is hereby incorporated by reference in its entirety.

In some embodiments according to the invention, the viral vector may be a lentiviral, retroviral, adenoviral, or Herpes Simplex Virus vector.

In this specification the term "operably linked" may include the situation where a selected nucleic acid sequence and regulatory nucleic acid sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleic acid sequence if the regulatory sequence is capable of effecting transcription of the nucleic acid sequence. Where appropriate, the resulting transcript may then be translated into a desired polypeptide.

The present invention provides methods for producing a T cell. In some embodiments, the methods are not practised on the human or animal body. In some embodiments, the methods are performed in vitro. In some embodiments, the methods are performed ex vivo.

It will be appreciated that the methods for producing a T cell according to the present invention are typically for producing more than one T cell. That is, the methods typically are typically for producing a population or preparation of T cells.

Methods for producing a T cell in accordance with the present invention may comprise modifying a T cell to express or comprise a TCR specific for a virus. In some embodiments, modification may comprise introducing a nucleic acid or vector according to the present disclosure into a T cell. In some embodiments, the methods additionally comprise culturing the T cell under conditions suitable for expression of the nucleic acid or vector by the T cell.

In some embodiments, introducing a nucleic acid or vector comprises transduction, e.g. retroviral transduction. Accordingly, in some embodiments the isolated nucleic acid or vector is comprised in a viral vector, or the vector is a viral vector. In some embodiments, the method comprises introducing a nucleic acid or vector according to the invention by electroporation, for example as described in Koh et al., Molecular Therapy—Nucleic Acids (2013) 2, e114, which is hereby incorporated by reference in its entirety.

In some embodiments, modification may be of a non-activated T cell. In some embodiments, modification of a T cell to express or comprise a TCR specific for a virus may not cause activation of the T cell being modified. In particular embodiments, the method comprises modifying a non-activated T cell to express or comprise a TCR specific for a virus, wherein following modification, the T cell is retains a non-activated phenotype and/or does not have an activated phenotype. Non-activated and activated T cell phenotypes can be defined by reference to expression of particular genes and/or proteins or by reference to certain activities for the T cell, as described herein.

In some embodiments, modification is by a method not requiring host cell division for effective uptake and/or expression of the nucleic acid. In particular embodiments, modification of a T cell (e.g. a non-activated T cell) is by mRNA electroporation. A T cell can be modified by mRNA electroporation with nucleic acid encoding a TCR for example as described in Example 5 herein.

Advantageously, mRNA electroporation does not require cell division for effective uptake and/or expression of the nucleic acid, and is therefore capable of introducing nucleic acid encoding a TCR as described herein into a slowly dividing or non-dividing cell, such as a non-activated T cell.

Methods for producing a T cell in accordance with the present invention may comprise modifying a T cell for reduced expression and/or activity of a cytotoxic factor.

In some embodiments, the cytotoxic factor is one or more of perforin, granzyme (e.g. granzyme B or granzyme A), granulysin, or FASL. In some embodiments, the cytotoxic factor is perforin and/or granzyme (e.g. granzyme B or granzyme A). After modification of the T cell for reduced expression and/or activity of the cytotoxic factor, the modified T cell may display a level of expression and/or activity of the cytotoxic factor which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the level of expression/activity by a reference cell, e.g. a comparable cell which has not been modified for reduced expression and/or activity of the cytotoxic factor.

Expression may be protein or gene expression. Gene expression of a cytotoxic factor can be determined e.g. by measuring levels of mRNA, for example by quantitative real-time PCR (qRT-PCR), or by reporter-based methods. Protein expression can be measured e.g. by western blot, immunohistochemistry, immunocytochemistry, flow cytometry, ELISA, etc., or by reporter-based methods. Activity of a cytotoxic factor analysed e.g. using an in vitro assay for the activity of the cytotoxic factor, e.g. an assay described in Zaritskaya et al., Expert Rev Vaccines (2011), 9(6):601-616, incorporated by reference hereinabove.

In some embodiments, modification may be by treatment with an agent capable of reducing expression and/or activity of a cytotoxic factor. In some embodiments, the agent may effect reduced gene or protein expression and/or activity by influencing transcription, mRNA processing (e.g. splicing), mRNA stability, translation, post-translational processing, protein stability, protein degradation and/or protein function/activity.

In some embodiments, the agent may be an agent which effects the amount of mRNA of the cytotoxic factor. In some embodiments, the agent may cause reduced expression of the cytotoxic factor by RNA interference (RNAi). In some embodiments, the agent may be an inhibitory nucleic acid, such as antisense or small interfering RNA, including but not limited to shRNA or siRNA. In some embodiments the inhibitory nucleic acid is provided in a vector. For example, in some embodiments the agent may be a lentiviral vector encoding shRNA for one or more cytotoxic factor.

In some embodiments the agent may be an agent capable of altering the genome of the T cell to reduce gene or protein expression and/or activity of the cytotoxic factor by the T cell. For example, the agent may be capable of disrupting and/or inactivating a gene encoding perforin, granzyme (e.g. granzyme B or granzyme A), granulysin, or FASL, and/or may integrate a DNA sequence encoding a sequence encoding a molecule capable of reducing perforin, granzyme (e.g. granzyme B or granzyme A), granulysin, or FASL gene or protein expression and/or activity.

In some embodiments the agent may be an inhibitor of perforin, granzyme (e.g. granzyme B or granzyme A), granulysin, or FASL protein. For example, the agent may be a molecule capable of binding to a cytotoxic factor and inhibiting its activity. In some embodiments the agent may be an antibody directed against perforin, granzyme (e.g. granzyme B or granzyme A), granulysin, or FASL. In some embodiments, the agent may be a competitive inhibitor of perforin, granzyme (e.g. granzyme B or granzyme A), granulysin, or FASL activity.

The present invention also includes a T cell which has been modified to reduce expression and/or activity of a cytotoxic factor. In some embodiments, the T cell has been modified with an agent capable of reducing expression and/or activity of a cytotoxic factor. Also provided is a T cell which contains an agent capable of reducing expression and/or activity of a cytotoxic factor.

In some embodiments, the T cell which is modified and/or treated with an agent in accordance with the various aspects of the invention is a CD3+ T cell. In some embodiments, the T cell is a CD3+, CD8+ T cell. In some embodiments, the T cell is a CD3+, CD4+ T cell. In some embodiments, the T cell is non-activated T cell. In some embodiments the T cell is an activated T cell. In some embodiments, the T cell is a cytotoxic T cell. In some embodiments the T cell is a T helper cell.

Any suitable T cell may be used in accordance with the methods of the present invention. In some embodiments, the T cell may be obtained from a donor. In some embodiments, the donor may be suffering from, or at risk of, a disease condition, such as viral, bacterial or fungal infection or cancer. In some embodiments, the donor may be healthy and/or not at particular risk of a disease condition.

In some embodiments, the T cell may comprise an HLA allele encoding a MHC class I molecule capable of presenting the peptide of the virus for which a TCR of the T cell is specific. In some embodiments the T cell is HLA matched for the viral peptide recognised by a TCR of the T cell. In some embodiments the T cell is obtained from a donor who is HLA matched for the viral peptide recognised by a TCR of the T cell.

The T cell may be isolated or otherwise obtained from appropriate samples from the donor e.g. samples from lymphoid tissue such as spleen or lymph nodes or from blood or tumour samples. Suitable isolation techniques are well known in the art and include, for example fluorescent activated cell sorting (FACS: see for example, Rheinherz et al (1979) PNAS 76 4061), cell panning (see for example, Lum et al (1982) Cell Immunol 72 122) and isolation using antibody coated magnetic beads (see, for example, Gaudernack et al 1986 J Immunol Methods 90 179). Conveniently, T cell subsets may be isolated using antibodies to cell surface markers; e.g. anti-CD8 antibodies may be used to isolate CD8+ T cells, and CD4+ T cells may be isolated using anti-CD4 antibodies. For example, the sample may be incubated with magnetic beads coated with antibodies, and the beads isolated using magnetic separation.

In some embodiments, the T cell which is modified and/or treated with an agent in accordance with the various aspects of the invention may be comprised in a sample of cells from a donor individual. The sample of cells may be a heterogeneous sample comprising other cell types, such as B cells, dendritic cells and macrophages, in addition to the T cell.

In some embodiments, a method described herein may comprise activating T cells. A T cell may be activated by any convenient technique. In some embodiments, a T cell may be activated by treatment with an agonist for the TCR of the T cell, such as a peptide displayed on a MHC class I molecule on the surface of an APC. In some embodiments a T cell may be activated with anti-CD3 and/or IL-2 (e.g. by culture in vitro).

In accordance with various aspects, the methods of the present invention may comprise culturing T cells ex vivo. The methods of the present invention may comprise culturing T cells in vitro.

T cells may be cultured in any suitable system, including stirred tank fermenters, airlift fermenters, roller bottles, culture bags or dishes, and other bioreactors. The use of such systems is well-known in the art.

Culture media suitable for use in the in vitro culture of T cells are available, in particular complete media, such as AIM-V, Iscoves medium and RPMI-1640 (Invitrogen-GIBCO). The medium may be supplemented with other factors such as serum, serum proteins and selective agents. For example, in some embodiments T cells are cultured in AIM-V+2% human AB serum. Conveniently, cells are cultured at 37° C. in a humidified atmosphere containing 5% $CO_2$ in a suitable culture medium.

The present invention also provides T cells obtained or obtainable by the methods for producing a T cell according to the present invention.

Medical Uses and Methods of Treatment and Prophylaxis

The T cells according to the present invention find use in therapeutic and prophylactic methods. The present invention includes pharmaceutical compositions comprising a T cell according to the present invention and a pharmaceutically acceptable carrier, adjuvant, excipient, or diluent.

It will be appreciated that the therapeutic and prophylactic methods of the invention typically comprise administration/use of more than one T cell according to the invention. That is, the therapeutic and prophylactic methods of the invention typically comprise administration/use of a population or preparation of T cells according to the invention.

In one aspect the present invention provides a T cell or pharmaceutical composition according to the present invention for use in a method of treating or preventing a disease or disorder.

In another aspect, the present invention provides the use of a T cell or pharmaceutical composition according to the present invention for use in the manufacture of a medicament for use in a method of treating or preventing a disease or disorder.

In another aspect, the present invention provides a method of treating or preventing a disease or disorder comprising administering to a subject a therapeutically or prophylactically effective amount of a T cell or pharmaceutical composition according to the present invention.

In particular, the T cell or pharmaceutical composition according to the present invention finds use to prevent or treat a disease which is caused or exacerbated by a viral infection, or a disease or disorder for which a viral infection is a risk factor.

The disease or disorder to be treated or prevented in accordance with the invention is selected based on the specificity of the T cell and/or TCR thereof.

The disease or disorder to be treated or prevented in accordance with the invention may be selected from a disease or disorder which is caused or exacerbated by a viral infection. Herein, a viral infection may be infection with a dsDNA virus (e.g. adenovirus, herpesvirus, poxvirus), ssRNA virus (e.g. parvovirus), dsRNA virus (e.g. reovirus), (+)ssRNA virus (e.g. picornavirus, togavirus), (−)ssRNA virus (e.g. orthomyxovirus, rhabdovirus), ssRNA-RT virus (e.g. retrovirus), dsDNA-RT virus (e.g. hepadnavirus), a member of the family adenoviridae, herpesviridae, papillomaviridae, polyomaviridae, poxviridae, hepadnaviridae, parvoviridae, astroviridae, caliciviridae, picornaviridae, coronaviridae, flaviviridae, togaviridae, hepeviridae, retroviridae, orthomyxoviridae, arenaviridae, bunyaviridae, filoviridae, paramyxoviridae, rhabdoviridae or reoviridae, Herpes simplex type 1 virus, Herpes simplex type 2 virus, Varicella-zoster virus, Epstein-barr virus, Human cytomegalovirus, Human herpesvirus type 8, Human papillomavirus, BK virus, JC virus, Smallpox, Hepatitis B virus (genotype A, B, C, D, E, F, G, H, I or J), Parvovirus B19, Human Astrovirus, Norwalk virus, coxsackievirus, hepatitis A virus, poliovirus, rhinovirus, severe acute respiratory syndrome virus, hepatitis C virus, yellow fever virus, dengue virus, West Nile virus, TBE virus, Rubella virus, Hepatitis E virus, Human immunodeficiency virus, influenza virus, lassa virus, Crimean-Congo hemorrhagic fever virus, Hantaan virus, ebola virus, Marburg virus, measles virus, mumps virus, parainfluenza virus, respiratory syncytial virus, rabies virus, hepatitis D virus, rotavirus, orbivirus, coltivirus, or banna virus, or a disease or disorder for which infection with such virus is a risk factor.

For example, where the T cell according to the invention comprises a TCR specific for hepatitis B virus, then the T cell or pharmaceutical composition according to the invention finds use to prevent or treat a disease or disorder which is caused or exacerbated by HBV infection, or a disease or disorder for which HBV infection is a risk factor. Diseases and disorders which are caused/exacerbated by HBV infection are described in Liang, Hepatology (2009), 49(5 Suppl): S13-S21, and include acute hepatitis (including fulminant hepatic failure), chronic hepatitis, cirrhosis, liver cancer such as hepatocellular carcinoma (HCC), or pancreatic cancer. Diseases and disorders for which HBV infection is a risk factor include necrotizing vasculitis and nephropathy such as membranous glomerulonephritis (MGN).

Administration of a T cell or pharmaceutical composition according to the invention is preferably in a "therapeutically effective" or "prophylactically effective" amount, this being sufficient to show benefit to the subject. The actual amount administered, and rate and time-course of administration, will depend on the nature and severity of the disease or disorder. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In embodiments of the present invention, a method of treatment or prophylaxis may comprise adoptive transfer of T cells. Adoptive T cell transfer generally refers to a process by which T cells are obtained from a subject, typically by drawing a blood sample from which T cells are isolated. The T cells are then typically treated or altered in some way, and either to the same subject or to a different subject. The treatment is typically aimed at providing a T cell population with certain desired characteristics to a subject, or increasing the frequency of T cells with such characteristics in that subject. Adoptive transfer of virus specific T cells is described, for example, in Cobbold et al., (2005) J. Exp. Med. 202: 379-386 and Rooney et al., (1998), Blood 92:1549-1555, hereby incorporated by reference in its entirety.

In the present invention, adoptive transfer is performed with the aim of introducing, or increasing the frequency of, virus-specific, antiviral T cells in a subject, in particular CD8+ T cells and/or CD4+ T cells.

Accordingly, in one aspect, the present invention provides a method of treating or preventing a disease or disorder in a subject, comprising:
(a) isolating at least one non-activated T cell from a subject;
(b) modifying the at least one non-activated T cell to express or comprise a T Cell Receptor (TCR) specific for a virus; and
(c) administering the modified at least one non-activated T cell to the subject;
wherein the modified at least one non-activated T cell displays reduced cytotoxicity against cells infected with, or comprising a peptide of, the virus as compared to an activated T cell comprising a TCR specific for the virus which is not modified for reduced expression or activity of a cytotoxic factor.

In another aspect, the present invention provides a method of treating or preventing a disease or disorder in a subject, comprising:

(a) isolating at least one T cell from a subject;
(b) modifying the at least one T cell to express or comprise a T Cell Receptor (TCR) specific for a virus, wherein:
    (i) the T cell is modified for reduced expression or activity of a cytotoxic factor, or
    (ii) the method further modifying the at least one T cell for reduced expression or activity of one or more cytotoxic factor; and
(c) administering the modified at least one T cell to the subject.

In another aspect, the present invention provides a method of treating or preventing a disease or disorder in a subject, comprising:

(a) isolating at least one T cell from a subject;
(b) modifying the at least one T cell for reduced expression or activity of one or more cytotoxic factor; and
(c) administering the modified at least one T cell to the subject.

In accordance with the present invention, "a subject" may be any subject. In some embodiments, the subject from which the T cell is isolated is the subject administered with the modified T cell. That is, in some embodiments the source of the T cell can be autologous. In some embodiments the subject from which the T cell is isolated may be a different subject to the subject administered with the modified T cell. That is, in some embodiments, the source of the T cell can be allogenic. In some embodiments, the T cell can be exogenous. In some embodiments the T cell can be xenogenic.

The at least one T cell modified according to the present invention can for example be modified according to methods described herein, e.g. to express or comprise a TCR specific for a virus and/or for reduced expression or activity of a cytotoxic factor. The modification may comprise nucleic acid transfer for permanent or transient expression of the transferred nucleic acid.

Any suitable genetic engineering platform may be used to modify a T cell according to the present invention. Suitable methods for modifying a T cell include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, incorporated by reference hereinabove.

In some embodiments the method may comprise one or more of the following steps: taking a blood sample from a subject; isolating at least one T cell (e.g. at least one non-activated T cell) from the blood sample; culturing the at least one T cell in in vitro or ex vivo cell culture; modifying the at least one T cell to express or comprise a TCR specific for a virus; modifying the at least one T cell for reduced expression or activity of a cytotoxic factor; collecting the at least one T cell; mixing the modified T cell with an adjuvant, diluent, or carrier; administering the modified T cell to a subject.

In some embodiments of the methods herein a method may comprise the step of activating a T cell, e.g. by stimulation through CD3/CD28 and/or by contact with APCs presenting peptide-MHC for which the T cell comprises a specific TCR, optionally in the presence of IL-2.

The skilled person is able to determine appropriate reagents and procedures for adoptive transfer of T cells according to the present invention for example by reference to Qasim et al., Journal of Hepatology (2015) 62: 486-491, which is incorporated by reference in its entirety.

The at least one modified T cell is typically administered to the subject as a population of cells. In some embodiments, one of about $1 \times 10^4$, $5 \times 10^4$, $1 \times 10^5$, $5 \times 10^5$, $1 \times 10^6$, $2 \times 10^6$, $5 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, or $1 \times 10^{10}$ cells are administered to the subject.

In some embodiments, the population of cells is a population of modified T cells. In some embodiments, the population of cells administered to the subject as a mixed population of cells. The mixed population of cells may comprise e.g. Natural Killer (NK) cells, non-modified T cells and/or Dendritic Cells (DCs) in addition to the modified T cells.

The population of cells administered to the subject may comprise a T cell population having different proportions of CD8+ and CD4+ T cells. For example, in some embodiments, the T cell population administered to the subject may comprise about 100% CD8+ T cells and 0% CD4+ T cells, about 95% CD8+ T cells and 5% CD4+ T cells, about 90% CD8+ T cells and 10% CD4+ T cells, about 85% CD8+ T cells and 15% CD4+ T cells, about 80% CD8+ T cells and 20% CD4+ T cells, about 70% CD8+ T cells and 30% CD4+ T cells, about 60% CD8+ T cells and 40% CD4+ T cells, or about 50% CD8+ T cells and 50% CD4+ T cells.

Administration is typically by infusion (e.g. intravenous infusion) of a population of cells. The population of cells is formulated as appropriate for administration by infusion.

The methods according to the present invention may involve more than one administration. That is, in some embodiments the methods may comprise multiple administrations of at least one modified T cell to the subject.

In embodiments according to the present invention the subject is preferably a human subject. In some embodiments, the subject to be treated according to a therapeutic or prophylactic method of the invention herein is selected based on HLA genotype. In some embodiments, the subject has an HLA allele encoding an MHC class I α-chain which in the context of an MHC class I molecule is capable of presenting a peptide of a virus for which the TCR of the T cell according to invention is specific.

In embodiments according to the present invention, a subject may be selected for a treatment of a disease or disorder caused or exacerbated by a viral infection, or a disease or disorder for which a viral infection is a risk factor based on characterisation for certain markers of such disease/disorder, e.g. a viral infection. A subject may have been diagnosed with the disease or disorder requiring treatment, or be suspected of having such a disease or disorder. In embodiments according to the present invention, a subject may be selected for a prophylactic method herein for the prevention of a disease or disorder caused or exacerbated by a viral infection, or a disease or disorder for which a viral infection is a risk factor based on characterisation for certain risk factors for a viral infection.

In embodiments according to various aspects of the present invention, treating or preventing a disease or disorder according to the present invention may comprise combination therapy. In such embodiments, a T cell or pharmaceutical composition according to the present invention may be administered as part of a course comprising further intervention.

In some embodiments, the method comprises intervention—e.g. through administration of a suitable agent—for the prevention or treatment of a viral infection, or a disease or disorder caused or exacerbated by a viral infection. Prophylactic intervention may comprise vaccination.

Suitable therapeutic agents can be readily identified by the skilled person as appropriate to the particular viral infection. suitable agents include one or more antiviral agents selected from abacavir, aciclovir, acyclovir, adefovir, amantadine, amprenavir, ampligen, arbidol, atazanavir, atripla, balavir, cidofovir, combivir, dolutegravir, darunavir, delavirdine, didanosine, docosanol, edoxudine, efavirenz, emtricitabine, enfuvirtide, entecavir, ecoliever, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitors, interferon type III, interferon type II, interferon type Id, interferon, lamivudine, lopinavir, loviride, maraviroc, moroxydine, methisazone, nelfinavir, nevirapine, nexavir, nitazoxanide, nucleoside analogues, novir, oseltamivir (tamiflu), PEG-interferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, sofosbuvir, stavudine, synergistic enhancers, telaprevir, tenofovir, tenofovir disoproxil, tipranavir, trifluridine, trizivir, tromantadine, truvada, valaciclovir (valtrex), valganciclovir, vicriviroc, vidarabine, viramidine, zalcitabine, zanamivir (relenza), and zidovudine.

For example, in the case of infection with hepatitis B virus, suitable agents include those described in the WHO Guidelines for the prevention, care and treatment of persons with chronic hepatitis B infection, March 2015, ISBN 9789241549059, and Alberti and Caporaso, Dig Liver Dis, 2011 43 Suppl 1: S57-63, which are both hereby incorporated by reference in their entirety. In particular, the present invention contemplates use of antiviral agents such as lamivudine (epivir), adefovir (hepsera), tenofovir (viread), telbivudine (tyzeka) and entecavir (baraclude), and combinations thereof, and also interferon alpha-2a and PEGylated interferon alpha-2a.

In some embodiments, the method comprises therapeutic or prophylactic intervention for the treatment or prevention of a cancer associated with viral infection, such as a hepatic cancer, e.g. hepatocellular carcinoma.

Patient Selection

The present invention also provides methods for identifying a subject for therapeutic or prophylactic treatment according to the invention.

In one aspect, a method for identifying a subject for therapeutic or prophylactic treatment comprises determining the HLA type for a subject. HLA typing can be performed by various methods well known to the skilled person, such as by sequencing the HLA gene or genes to by typed, and comparing the DNA sequence to sequences for known HLA alleles. In some embodiments, a subject determined to have a HLA allele encoding an MHC class I molecule capable of presenting a peptide of a virus recognised by the TCR of a T cell according to the present invention is identified as being a subject suitable for therapeutic or prophylactic treatment according to the invention.

In one aspect, a method for identifying a subject for therapeutic or prophylactic treatment comprises determining whether the subject is infected with, or is at risk of infection by, viral infection. Viral infection can be diagnosed by various methods well known to the skilled person, and include methods for the detection of viral nucleic acid and/or protein in a sample obtained from an individual. In some embodiments, a subject determined to be infected with a virus for which the T cell according to the present invention comprises a specific TCR is identified as being a subject suitable for therapeutic or prophylactic treatment according to the invention.

Compositions

The present invention also provides compositions comprising a T cell according to the present invention. In some embodiments, the composition is a pharmaceutical composition. In some embodiments, the composition is a composition suitable for use in research, therapy, prophylaxis and/or diagnosis.

It will be appreciated that compositions according to the invention will typically comprise more than one T cell according to the invention. That is, the compositions will typically comprise a population or preparation of T cells according to the invention.

In some embodiments, a T cell according to the present invention preferably formulated as a medicament or pharmaceutical together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation. Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulations may be prepared for administration by a number of routes. The medicaments and compositions may be formulated in fluid or solid (including powder) form. The route for administration may be topical, parenteral, systemic, intravenous, intra-arterial, intramuscular, intrathecal, intraocular, subcutaneous, oral or transdermal. In some embodiments, administration may include injection. Injectable formulations may comprise the selected agent in a sterile or isotonic medium.

In one aspect of the present invention a kit of parts is provided, comprising a predetermined quantity of a T cell or pharmaceutical composition according to the present invention. In some embodiments, the kit may include instructions for using T cell or pharmaceutical composition in a method as described herein. For example, in some embodiments the kit may include instructions for administration of the T cell or pharmaceutical composition to a patient in order to treat or prevent a disease or disorder as described herein.

In another aspect a kit of parts is provided, comprising a nucleic acid encoding a TCR and an agent for reducing the expression or activity of a cytotoxic factor. In some embodiments, the kit may include instructions for using the nucleic acid and/or agent in a method as described herein. For example, in some embodiments the kit may include instructions for introducing the nucleic acid into a T cell and/or instructions for treating a T cell with the agent for reducing the expression or activity of a cytotoxic factor.

In some embodiments the kit may additionally include other materials and/or reagents for performing a method according to the present invention. For example, in some embodiments the kit may additionally include materials and/or reagents for introducing a nucleic acid into a T cell, and/or for culturing T cells in vitro.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which.

EXAMPLES

Figure 1A:
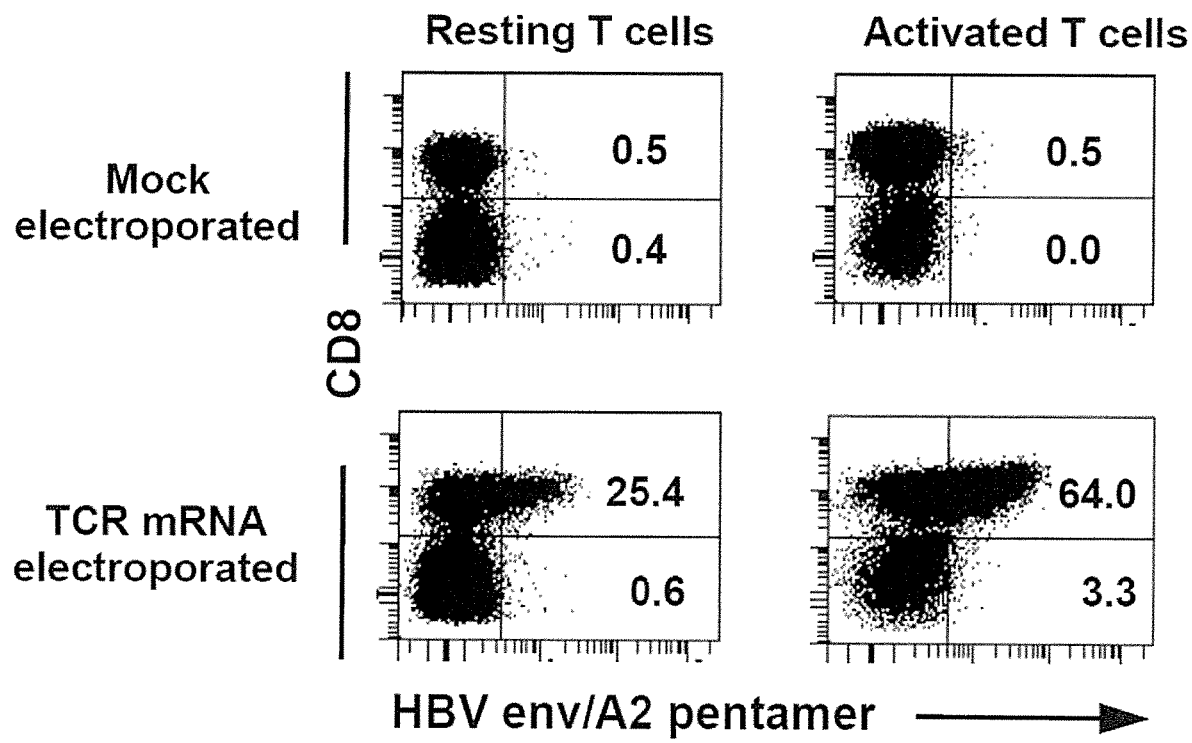
FIG. 1. Graphs showing HBV TCR expression on T cells. (A) scatterplots showing expression of HBV TCR on resting and activated T cells electroporated with mRNA encoding HBV TCR, as measured by pentamer staining. (B) Graphs showing the level of expression of the TCR over time following electroporation. MFI=mean fluorescence intensity.

The inventors describe in the following Examples the generation and characterisation of virus-specific T cells.

Example 1: Cell Lines

HepG2-Env and HepG2-Core expressing luciferase cell lines were cultured in RPMI 1640 supplemented with 10% heat-inactivated fetal bovine serum (FBS), 20 mM HEPES. 0.5 mM sodium pyruvate, 100 U/ml penicillin, 100 μg/ml streptomycin, MeM amino acids, Glutamax, MeM nonessential amino acids, (Invitrogen, Carlsbad, Calif.), and 2 μg/ml puromycin (BD Biosciences, San Jose, Calif.) was added to maintain selection. T2 cells were cultured in RPMI 1640 supplemented as described above. HepG2 cells that stably expressed the entire HBV genome and produced infectious virus (HepG2.2.15) were cultured in DMEM supplemented with 10% heat-inactivated FBS. 20 mM HEPES. 0.5 mM sodium pyruvate, and 150 μg/ml G418 (Sigma-Aldrich, St. Louis, Mo.). HepG2 cells that stably expressed human sodium taurocholate co-transporting polypeptide (hNTCP) were cultured in DMEM supplemented with 10% heat-inactivated FBS. Glutamax, 100 U/ml penicillin, 100 μg/ml streptomycin, and 5 μg/ml puromycin was added to maintain selection. Huh7 cells expressing HLA-A2 and harboring HCV replicon encoding luciferase were cultured in DMEM supplemented with 10% heat-inactivated FBS, Glutamax, MeM nonessential amino acids, 100 U/ml penicillin, 100 µg/ml streptomycin, 1 mg/ml G418 and 3 µg/ml blasticidin S hydrochloride were added to maintain selection.

Example 2: T Cells

Peripheral blood mononuclear cells (PBMC) were collected under informed consent from healthy donors. To produce activated T cells, PBMC were stimulated with 600 IU/ml interleukin-2 (rIL-2; R&D Systems) and 50 ng/ml anti-CD3 (OKT-3; eBioscience, San Diego, Calif.) in AIM-V+2% human AB serum for 8 days, and rIL-2 was increased to 1000 IU/ml one day before electroporation. Non-activated (resting) T cells were isolated using the pan T cell isolation kit (Miltenyi Biotec, GmbH, Germany) and cultured overnight in 100 IU/ml rIL-2 before electroporation.

Example 3: Flow Cytometry

Antibodies for cell surface staining were obtained from BD Biosciences (anti-human CD8-PE-Cy7, CD8-V500, CD45RA-APC, CD62L-PECy7), eBioscience (anti-human CD45RO-eFluor650), Immudex and Proimmune (HLA-A201-HBs183-91-PE dextramer or pentamer), and R&D Systems (human LTβ receptor-Fc chimera). Antibodies for intracellular cytokine staining were obtained from BD Biosciences (anti-human IFN-γ-APC, TNF-α-Alexa488, IL-2-PE, Granzyme-APC) and Diaclone (anti-human perforin-FITC). Intracellular cytokine staining was performed by fixing and permeabilizing cells with cytofix/cytoperm (BD Biosciences). Flow cytometry was performed using a FACS Canto flow cytometer or LSRII (BD Biosciences) and data was analyzed with FACS Diva program (BD Biosciences).

Example 4: Production of HBV Envelope s183-191 TCR mRNA

The HBV envelope s183-191 TCR construct (HBV s183-TCR) was derived from a pUC57-s183cys b2Aa vector, and sub-cloned it into the pVAX1 vector. Plasmids were propagated in and purified from $E.\ coli$ using the One Shot Top10 $E.\ coli$ kit (Invitrogen), purified using QIAGEN Endo Free Plasmid Maxi Kit (QIAGEN, Valencia, Calif.), and linearized using the XbaI restriction enzyme. The linearized DNA was used to produce the TCR mRNA using the mMESSAGE mMACHINE T7 Ultra Kit (Ambion, Austin, Tex.) or T7 mScript Standard mRNA Production System (Cellscript, Madison, Wis.); T7 RNA polymerase was added to start transcription; RNA was capped with Anti-Reverse Cap Analog (ARCA). Then, poly(A)-tail was added by $E.\ coli$ Poly(A) Polymerase and ATP. The resulting product was concentrated by lithium chloride precipitation and re-dissolved in buffer.

Example 5: mRNA Electroporation of T Cells

For electroporation with the 4D-nucleofector system (Lonza, Cologne, Germany), $10 \times 10^6$ activated T cells or non-activated (resting) T cells as described above were suspended in 100 µl of supplemented 4D-Nucleofector Solution at room temperature and HBV s183-TCR mRNA was added at 200 µg/ml. The mixture was placed in a nucleocuvette and electroporated using program for stimulated or unstimulated T cells. After electroporation, cells were resuspended in AIM-V 10% human AB serum+100 IU/ml rIL-2, and cultured at 37° C. and 5% $CO_2$ until analysis.

Example 6: Function of mRNA Electroporated T Cells

HLA-A2+ T2 cells were pulsed with 1 µg/ml of s183-191 peptide for 1 h at $10^6$ cells/ml and then washed twice. HBV s183-TCR mRNA electroporated activated (activated EP) or non-activated (resting EP) T cells were co-cultured with peptide-loaded T2 cells for 5 h or overnight in the presence of 10 µg/ml or 2 µg/ml brefeldin A respectively, and stained for CD8, IFN-γ, granzyme and perforin.

Example 7: Cytotoxicity Assays

HepG2-Core or HepG2-Env expressing luciferase cell lines were plated overnight in 96-well flat bottom plate to permit adherence. Target cells were washed and co-cultured with HBV s183-TCR mRNA electroporated activated or non-activated (resting) T cells at various effector:target (E:T) ratios (effectors calculated based on frequency of CD8+pentamer+ cells) in triplicates in AIM-V+2% human AB serum for 24 h. Cytotoxicity was measured by quantifying luciferase expression in remaining target cells. Briefly, culture medium was discarded and 100 µl of Steady-Glo reagent (Promega, Madison, Wis.) was added to each well and incubated for 5 min to allow cell lysis. Luminescence was measured with a microplate reader (Tecan, Mannedorf, Switzerland). Target cells without effectors were used as a reference for maximum luminescence. Results were expressed as % lysis=100%−(luminescence remaining after lysis/maximum luminescence) % and calculated as mean of triplicate measurements+/−standard deviation.

Example 8: Co-Culture Experiments of mRNA Electroporated T Cells with Targets HBV s183-TCR mRNA electroporated activated or non-activated (resting) T cells were co-cultured with either HepG2.2.15 or HBV-infected HepG2-hNTCP at 1:3 and 1:1 E:T ratios (effectors calculated based on frequency of CD8+ pentamer+ cells) for 24 h. HCV NS3 TCR mRNA electroporated non-activated (resting) T cells were co-cultured with Huh7 HCV replicon cells for 18 h, followed by quantification of luminescence as described above. To assess for target cell lysis after co-culture with T cells, supernatants from co-culture experiments were collected for measurement of alanine aminotransferase (ALT) after 24 h, or viability assays were performed using the Cell Proliferation Kit II (XTT) (Roche Applied Science, Mannheim, Germany). For blocking IFN-γ, 20 µg/ml purified anti-human IFN-γ or isotype control mouse IgG1 (BioLegend) was added. To block lymphotoxin (LT)α1β2, LTα2β1 and LIGHT, 1 µg/ml recombinant human LTβ receptor-Fc chimera (R&D Systems, Minneapolis, USA) was used.

Example 9: HBV Infection

Approximately 80 to 100-fold concentrated supernatant of HepAD38 cells was used as HBV inoculum. HepG2-hNTCP cells seeded overnight in 24-well plates were inoculated for 24 h with approximately multiplicities of genome equivalents of 3000/well HBV in medium containing 4% polyethylene glycol (Sigma-Aldrich). After infection, cells were washed with PBS 3 times and culture medium with DMSO was added and changed every 2 days. Viral infection was analysed by measuring hepatitis B surface antigen (HBsAg), hepatitis B core antigen (HBcAg) expression on infected cells by flow cytometry, and HBV DNA was quantified by real-time PCR.

Example 10: Quantification of HBV Genome Equivalent Copies

RLT buffer with β-mercaptoethanol or lysis buffer containing 50 mM Tris, 140 mM NaCl, 1.5 mM MgCl, 0.5% NP-40 at pH 8 was added to lyse the cells for isolation of intracellular viral nucleic acids using QIAamp MinElute Virus Spin kit (Qiagen, Valencia, Calif.), and HBV DNA was quantified by real-time PCR. Real-time PCRs were performed using the artus HBV RG PCR kit following the manufacturer's instructions in a Rotor-Gene Q 2-plex instrument Qiagen).

Example 11: Three-Dimensional Microdevice-Based Assay

To prepare 200 µl of a 2.5 mg/ml type-I collagen gel solution containing homogenously dissociated HepG2 targets, 20 µl of 1 OX PBS was mixed with 4 µl of NaOH (0.5 M), 129.2 µl of collagen type I (Rat Tail, Dow Corning), 20 µl of freshly trypsinized and dissociated HepG2 targets at $5 \times 10^6$ cells/ml and 22.9 µl of cell culture water. The final pH of the gel solution was approximately 7 as determined using a pH indicator strip. The collagen gel solution containing the HepG2 targets was then injected into the device dedicated gel region of the device and polymerized for 40 min in the cell culture incubator (37° C., 5% $CO_2$). Immediately after gel polymerization, the media channels were filled with R10 media in order to hydrate the gel and keep the HepG2 targets vital. The cell impermeable nuclear dye DRAQ7 (BioLegend, San Diego, Calif.) was also added in the R10 media at a concentration of 3 µM to discriminate between live and dead cells. The devices were then incubated for 24 hr to permit the interaction of the HepG2 targets with the collagen matrix.

Devices with empty gel regions (control) were prepared similarly by adding collagen gel solution containing 20 µl of 10× PBS, 4 µl of NaOH (0.5 M), 129.2 µl of collagen I and 42.8 µl of cell culture water. Prior to injection of the T cells in the device R10 media in the device was replaced with DRAQ7 containing AIM-V 2% human AB serum+100 IU/ml rIL-2.

In order to visualize the spatial position of the engineered T cells, the cells were stained with 3 µM of CellTracker Violet BMQC (Life Technologies Co., Carlsbad, Calif.) in RPMI 1640 for 30 min at 37° C. T cell suspensions were then washed with AIM-V 2% human AB serum, followed by another 30 min incubation at 37° C. The stained T cells were then washed, and resuspended in the corresponding media at $3 \times 10^6$ cells/ml. 30 µl of the T cell suspension was then added into one of two culture media channels flanking the central gel region of each device. Finally, the devices were incubated overnight in the indicated conditions.

Live imaging (time-lapse) experiments were performed using either the LSM7800 confocal microscope (Zeiss, Germany) or FV1200 confocal microscope (Olympus, Japan) equipped with an environmental chamber set at 37° C. and 5% $CO_2$. The microscope was programmed in order to acquire Z stacks of the selected regions at the stated time intervals. For static imaging experiments, confocal images of the same region of interest were acquired before T cell addition and after overnight incubation.

Example 12: Statistical Analysis

Statistical analysis was performed in GraphPad Prism (Graph-Pad Software Inc). For comparisons involving more than two groups, statistical significance was determined using the Kruksal Wallis test with Dunn's post-test for multiple comparisons with p<0.05 taken as evidence of a significant difference.

Example 13: Expression of HBV TCR on Human Non-Activated T Cells Using TCR mRNA Electroporation It is known that mRNA electroporation can introduce transgenes in human primary lymphocytes without any pre-activation (Zhao et al. Mol Ther (2006), 13 (1): 151-159). This could have significant advantages with respect to clinical applications.

The present inventors investigated whether HBV TCR could be expressed on unstimulated non-activated (resting) T cells.

mRNA encoding the alpha and beta chains of a HLA-A2-restricted HBV envelope s183-TCR was electroporated into unstimulated, non-activated (resting) T cells, or T cells which had been activated for 8 days with anti-CD3 and IL-2.

At 24 hours post-electroporation, 25% of non-activated (resting) T cells and 64% of activated T cells expressed the introduced HBV s183-TCR (FIG. 1A).

Figure 1B:
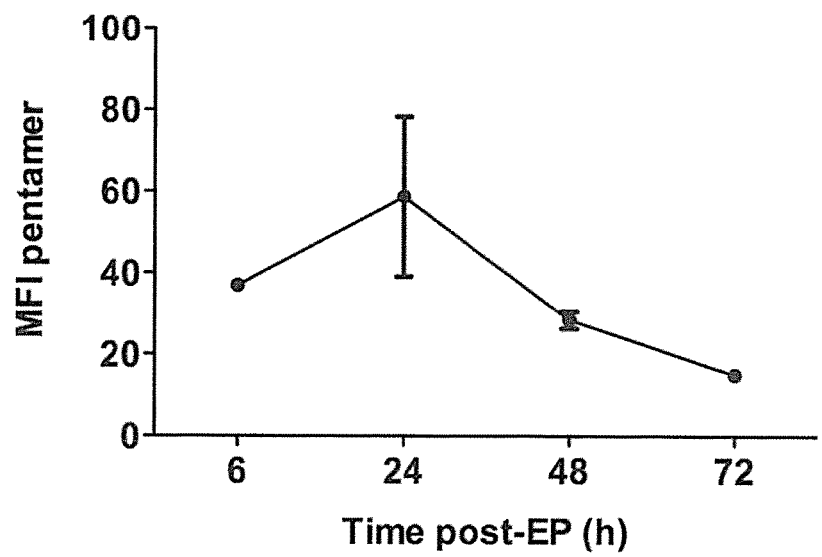

The Kinetics of TCR expression following electroporation was also determined. Similar to activated T cells, HBV s183-TCR expressed on non-activated (resting) T cells could be detected at 6 hours post-electroporation; TCR expression peaked at 24 hours post-electroporation and disappeared after 72 hours (FIG. 1B).

Example 14: Differentiation Phenotype of HBV TCR mRNA Electroporated T Cells

Preclinical animal models and retrospective analyses of human adoptive T cell therapy clinical trials have shown that infusion of less differentiated non-activated, stem cell memory or central memory T cell subsets can increase the therapeutic efficacy of adoptive T cell therapy (Klebanoff et al. J Immunother. (2012), 35(9): 651-660).

The present inventors therefore analyzed the differentiation phenotypes of both non-activated and activated T cells expressing the introduced HBV s183-TCR.

Figure 2A:
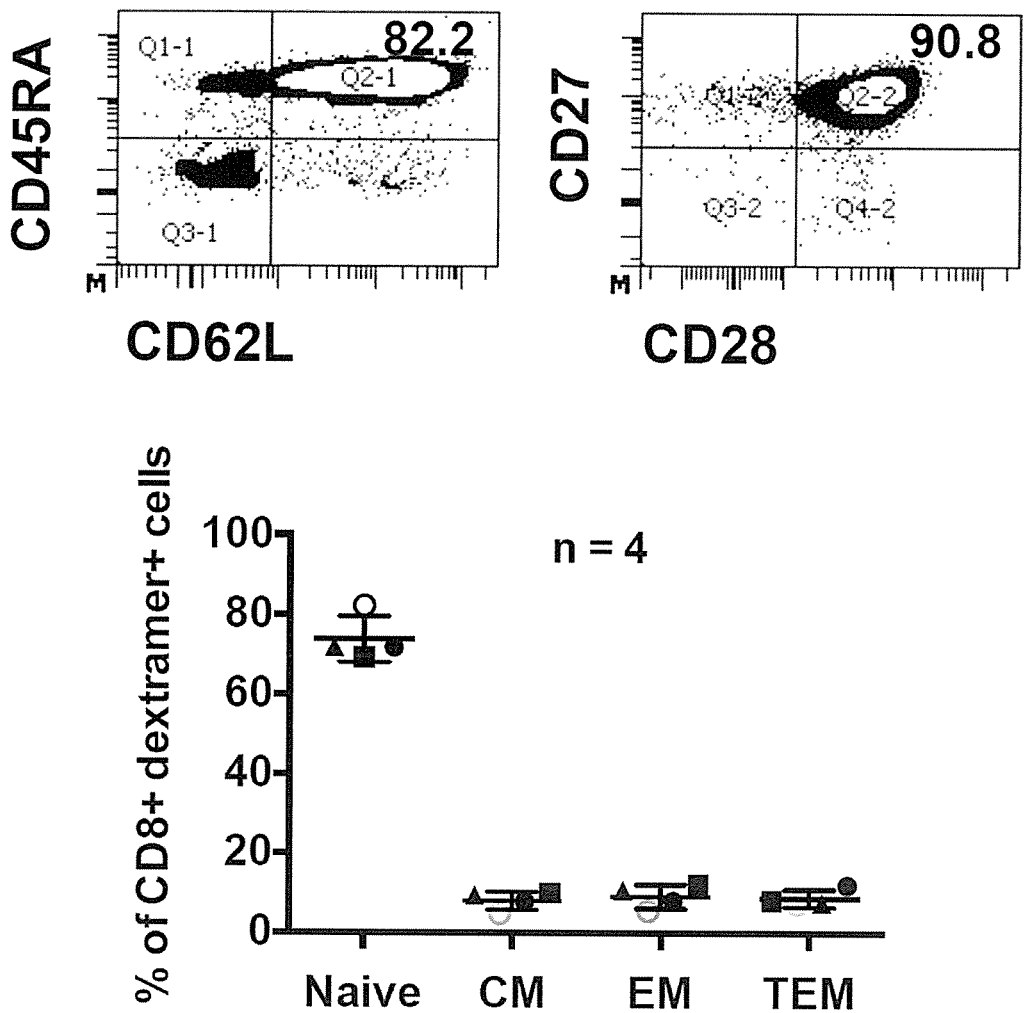
FIG. 2. Graphs showing phenotypes of T cells electroporated with HBV TCR mRNA. (A) scatterplots showing CD45RA, CD62L, CD27 and CD28 expression by electroporated resting T cells, and chart showing % of CD8+ dextramer+ cells amongst resting T cell subsets. (B) scatterplots showing CD45RA, CD62L, CD27 and CD28 expression by electroporated activated T cells, and chart showing % of CD8+ dextramer+ cells amongst activated T cell subsets. CM=central memory, EM=effector memory, TEM=Terminally effector memory.
Figure 2B:
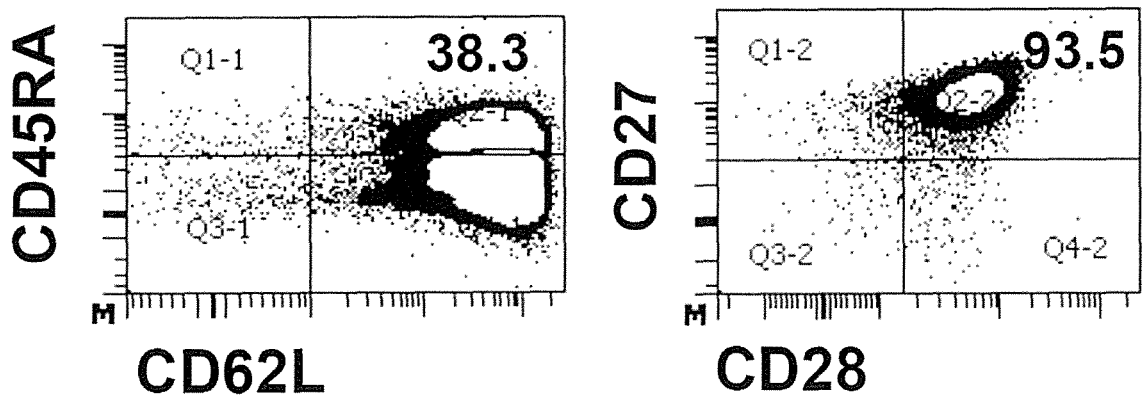
Figure 2B:
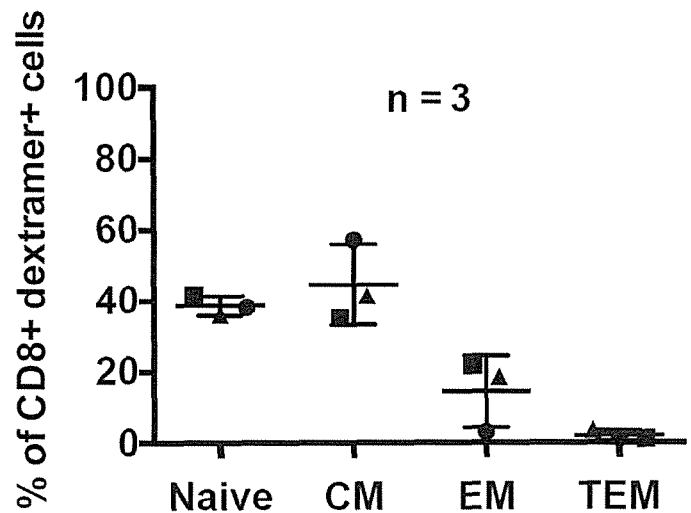
Figure 3A:
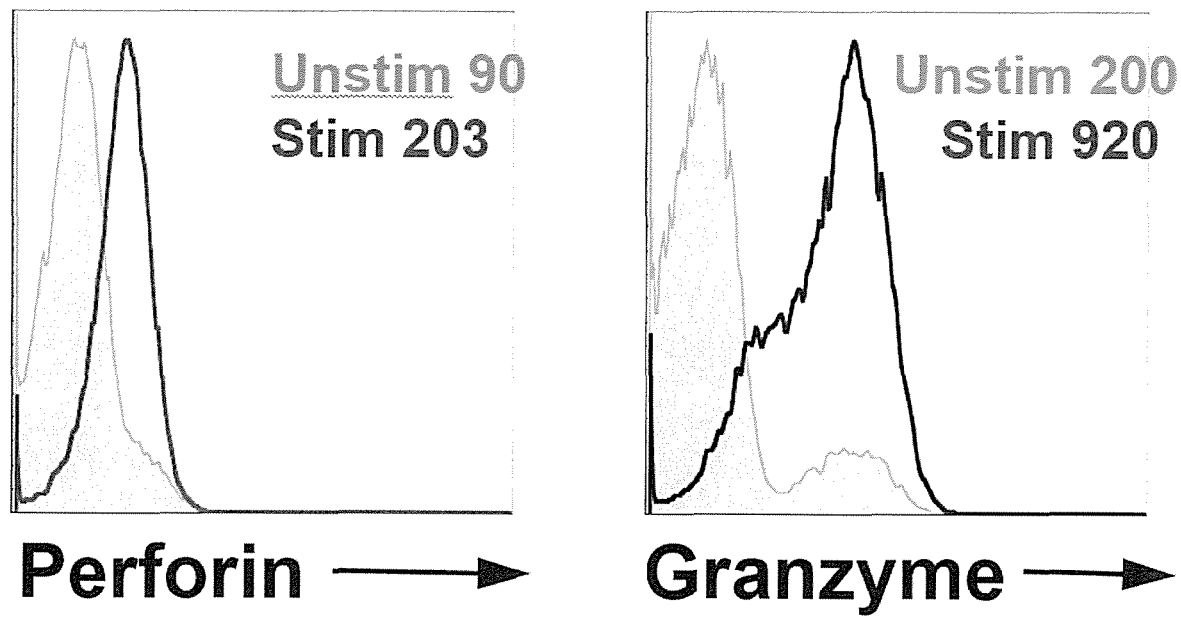
FIG. 3. Graphs showing expression of cytotoxic factors by T cells electroporated with HBV TCR mRNA. (A) Histograms showing expression of perforin and granzyme by electroporated, activated T cells stimulated with peptide with as compared to unstimulated activated, electroporated T cells. (B) Histograms showing expression of perforin and granzyme by electroporated, resting T cells stimulated with peptide as compared to unstimulated, resting electroporated T cells. (C) Chart showing the percentage of granzyme B+ CD8 cells of the total number of lymphocytes, (D) Chart showing the percentage of perforin+ CD8 cells of the total number of lymphocytes and (E) Chart showing the percentage of IFN-γ+ CD8 cells of the total number of lymphocytes, for activated, electroporated and resting, electroporated T cells, after 5 hours or 24 hours of peptide-specific stimulation, or in the absence of stimulation (unstimulated).
Figure 3B:
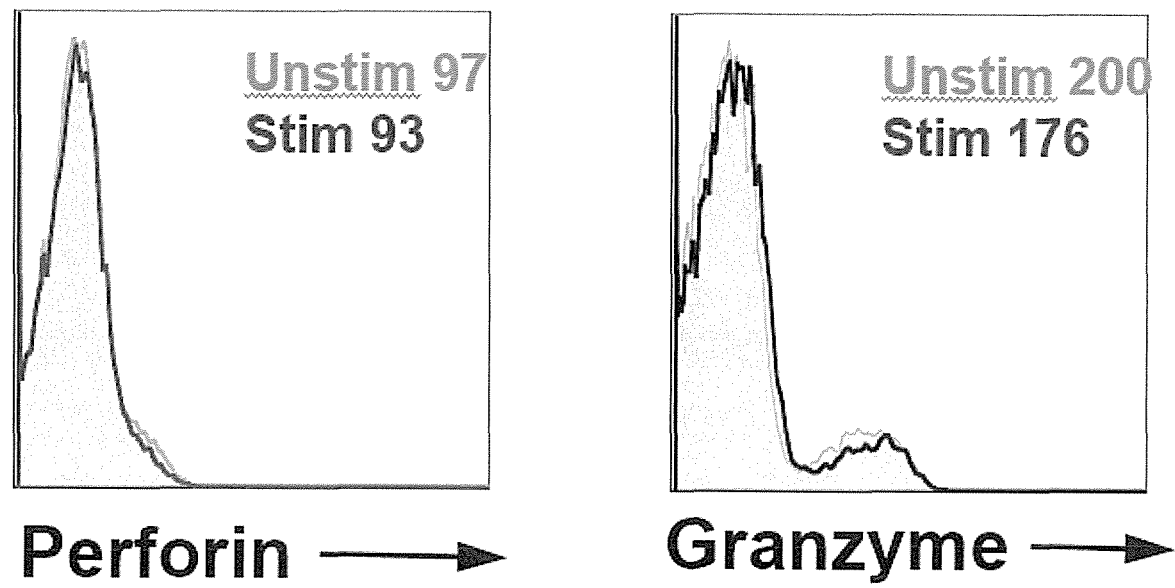
Figure 3C:
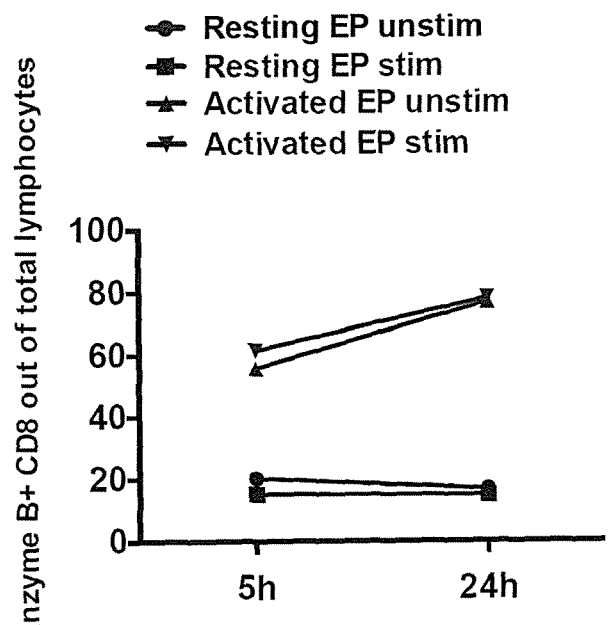
Figure 3D:
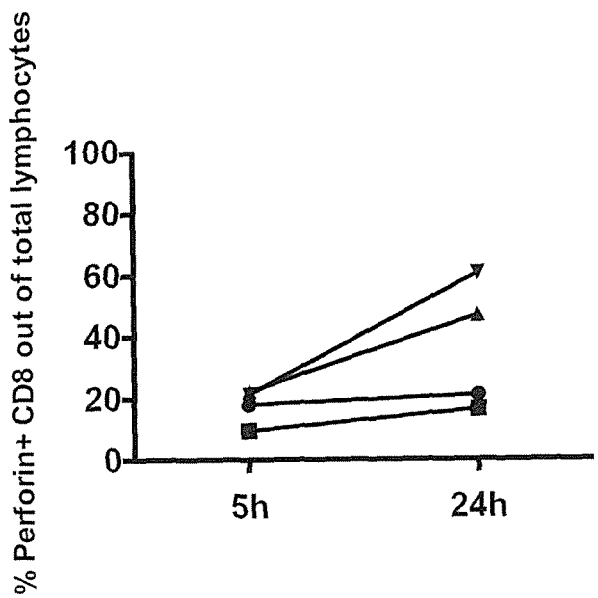
Figure 3E:
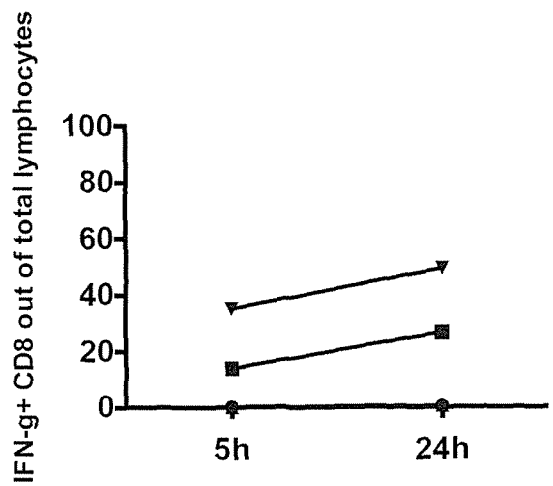

Whilst more than 80% of non-activated HBV s183-TCR T cells have a CD45RA+CD62L+ non-activated phenotype, activated HBV s183-TCR T cells comprise of a mixture of 40% CD45RA+CD62L+ non-activated, 45% CD45RA-CD62L+ central memory and 15% effector memory phenotypes (FIGS. 2A and 2B). More than 90% of both non-activated and activated HBV s183-TCR T cells expressed both costimulatory receptors CD27 and CD28 (FIGS. 2A and 2B), likely because electroporation can stimulate proliferation of cells (Qiabius et al. New Biotech (2015), 32(1): 229-235).

No difference was observed in the differentiation phenotypes of non-TCR expressing compared to TCR expressing cells within non-activated or activated T cells, indicating that mRNA electroporation does not preferentially transfect cells of particular differentiation status (data not shown).

Example 15: Analysis of Cytolytic Enzyme Production by HBV TCR mRNA Electroporated T Cells It is known that the expression of cytolytic enzymes (granzyme and perforin) and cytokines is related to T cell maturity and differentiation; non-activated (resting) T cells express little or no cytolytic enzymes and less cytokines compared with more differentiated cell types (Chattopadhyay et al., J Leukoc Biol (2009) 85(1): 88-97, incorporated by reference hereinabove). The inventors therefore analyzed the expression of granzyme B, perforin and IFN-γ in non-activated and activated HBV TCR mRNA-electroporated T cells after 5 hours and 24 hours of peptide-specific stimulation.

The results are shown in FIG. 3. Electroporated, activated T cells were found to express higher levels of perforin, granzyme B and IFN-γ than electroporated non-activated (resting) T cells.

Example 16: Analysis of Ability of HBV TCR mRNA Electroporated T Cells to Lyse Target Cells Electroporated, activated or non-activated (resting) T cells were investigated for their ability to lyse target cells. The amount of target cell killing was quantified using both static and live imaging.

Figure 4A:
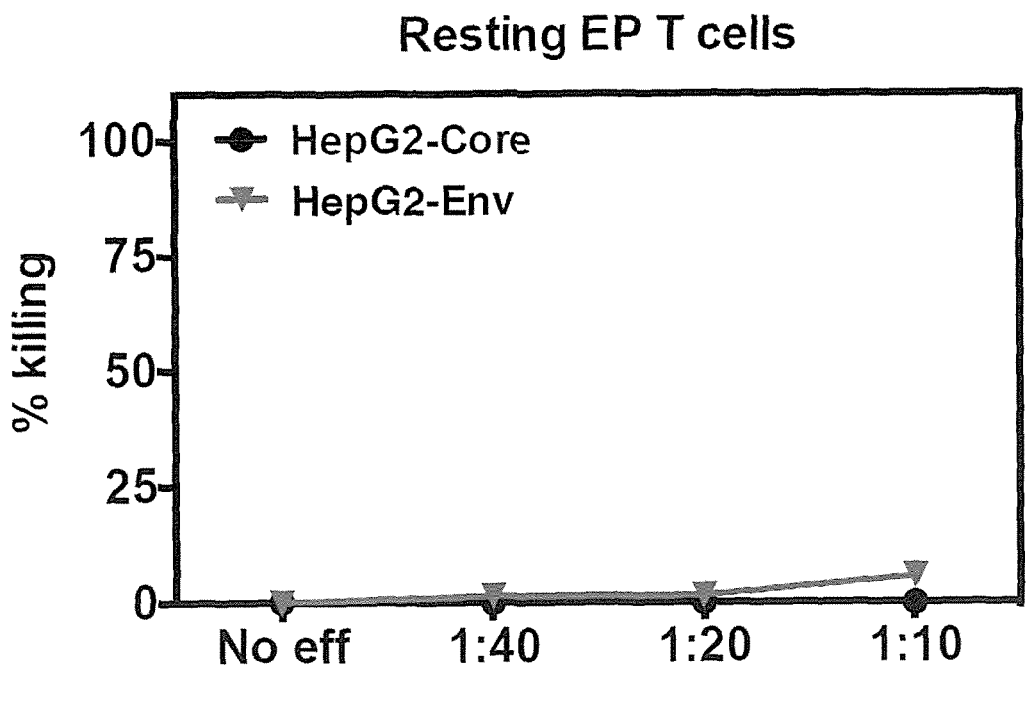
FIG. 4. Graphs and bar chart showing cytotoxicity of T cells electroporated with HBV TCR mRNA to cells expressing HBV antigens. (A) Graph showing % cell killing of cells expressing HBV antigen by resting, electroporated T cells at different effector:target cell ratios. (B) Graph showing % cell killing of cells expressing HBV antigen by activated, electroporated T cells at different effector:target cell ratios. (C) Bar chart showing % cell killing of cells expressing HBV Env antigen by activated, electroporated T cells, resting, electroporated T cells, activated, non-electroporated T cells and resting, non-electroporated T cells.
Figure 4B:
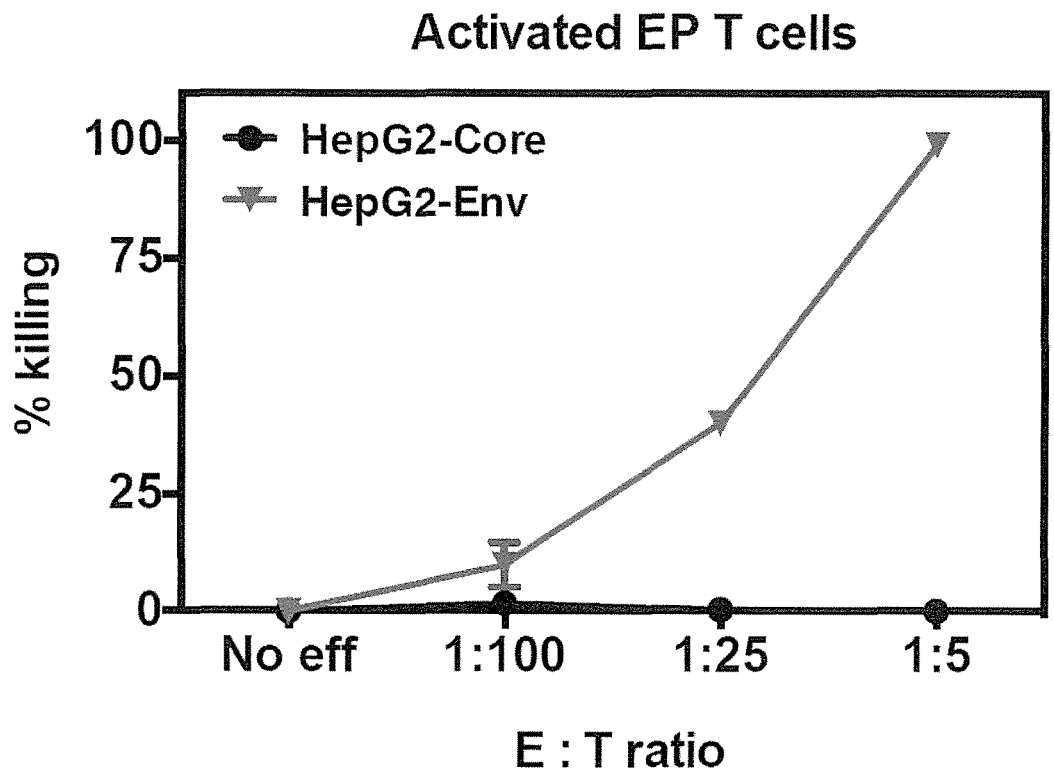
Figure 4C:
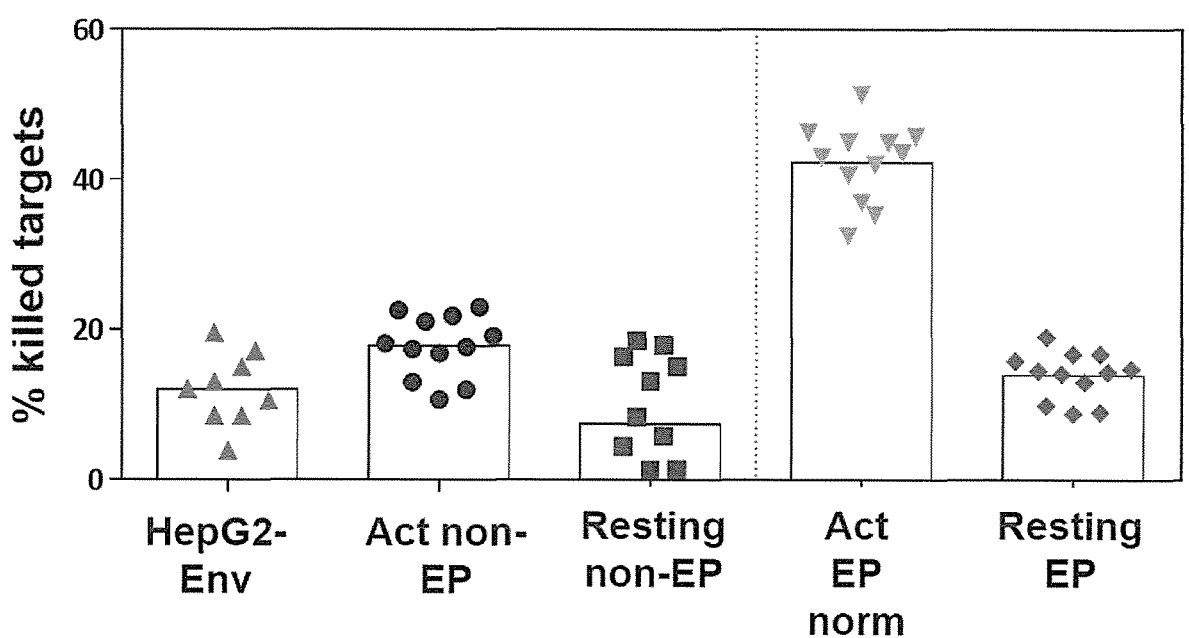

The results are shown in FIG. 4. Overnight co-culture of activated, electroporated T cells normalized to the same antigen specific frequency as non-activated, electroporated T cells were able to lyse targets. However, non-activated, electroporated T cells did not lyse target cells.

Figure 5:
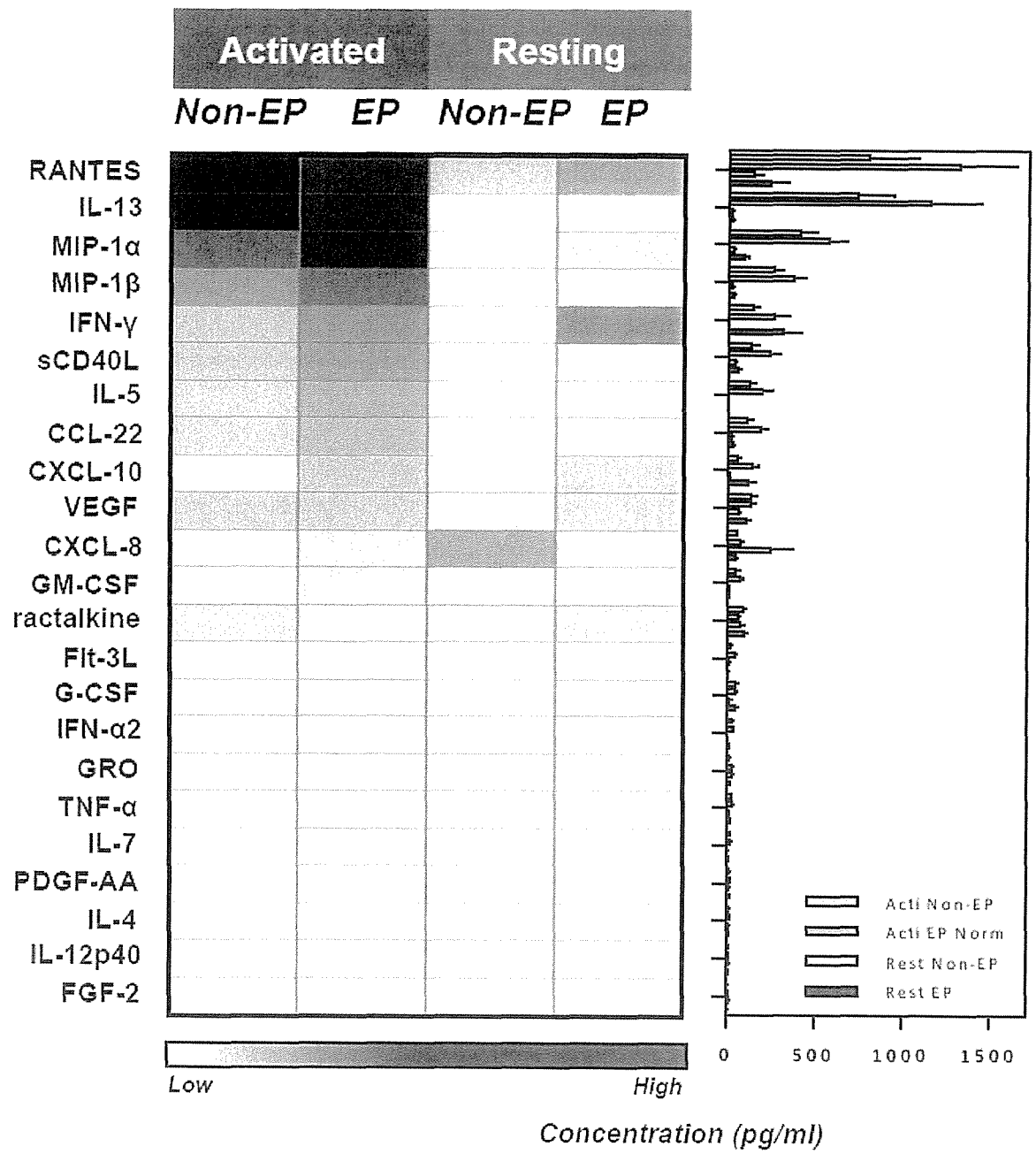
FIG. 5. Image and bar chart showing expression of various soluble factors by activated, electroporated T cells, resting, electroporated T cells, activated, non-electroporated T cells and resting, non-electroporated T cells.

Example 17: Analysis of Cytokine Production by HBV TCR mRNA Electroporated T Cells Electroporated, activated or non-activated T cells were analysed for expression of various cytokines, and the results are shown in FIG. 5.

Electroporated, activated T cells produced more RANTES, IL-13, MIP-1α and MIP-1β than electroporated, non-activated T cells. Non-electroporated activated T cells produced more RANTES, IL-13, MIP-1α and MIP-1β than electroporated non-activated T cells.

Example 18: Analysis of Antiviral Activity of HBV TCR mRNA Electroporated T Cells A HCV replicon system was used to analyse whether electroporated T cells exhibited antiviral activity without causing lysis of target cells.

Huh7 cells expressing HLA-A2 were transfected with a construct encoding the HCV JFH-1 strain and luciferase, described in Jo et al., Gastroenterology (2009) 136(4):1391-1401. Luciferase activity correlated with HCV RNA replication, and therefore viral replication could be analysed by measuring luminescence.

The cells were pulsed with 1 μg/ml HBV env 183 peptide overnight, and then co-cultured for 24 h with HBV env TCR electroporated activated or non-activated T cells. Peptide-pulsed HCV replicon cells were co-cultured with T cells at various effector:target (E:T) ratios, and antiviral activity was determined by calculating the percentage reduction in luminescence. Supernatants of the co-cultures were collected and analysed for aspartate aminotransferase (AST) as a marker of target cell lysis.

Figure 6A:
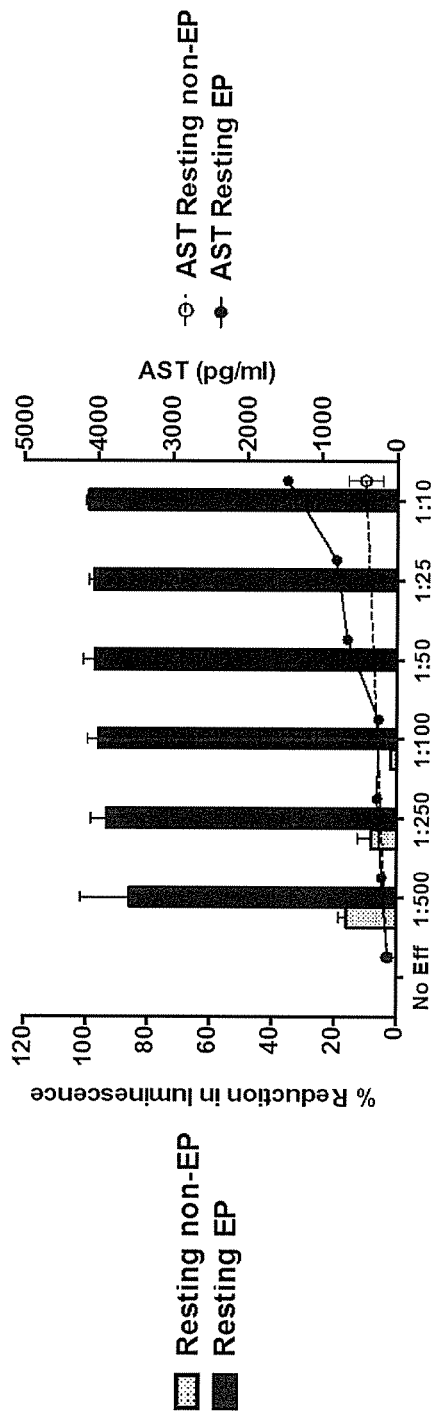
FIG. 6. Graphs showing antiviral activity and cytotoxicity of T cells to HCV replicon-infected liver cells at different effector:target cell ratios. Bars showing inhibition of viral replication as determined by % reduction of luminescence, and lines showing cytolysis as determined by aspartate aminotransferase (AST) levels. (A) resting, electroporated T cells and resting, non-electroporated T cells. (B) activated, electroporated T cells and activated, non-electroporated T cells.
Figure 6B:
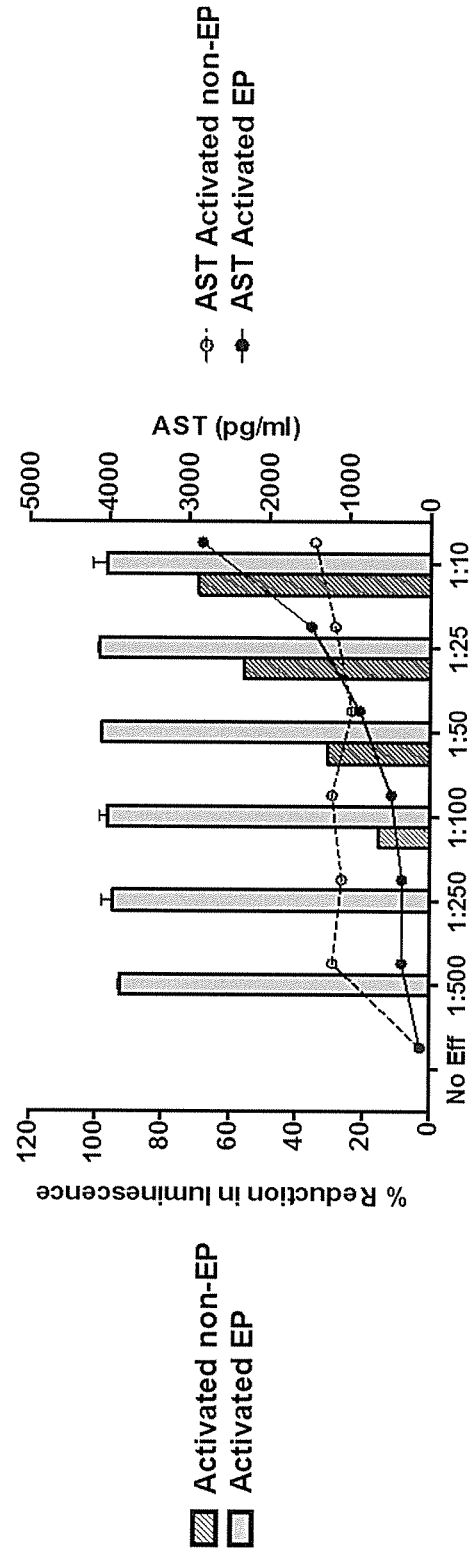

The results of the experiments are shown in FIGS. 6A and 6B. Both electroporated non-activated T cells and electroporated activated T cells were shown to have high antiviral activity, even at high E:T ratio. For example, even at E:T 1:500 a ~80% reduction in luminescence was observed.

Importantly, electroporated non-activated T cells were shown to possess this antiviral activity without extensive target cell lysis, as illustrated by detection of lower levels of AST in co-culture supernatant as compared to co-cultures with electroporated activated T cells.

Further co-culture experiments were performed using electroporated non-activated T cells (either as a bulk population, or subsets sorted based on surface marker expression) and HBV producing HepG2 cells at 1:3 E:T for 24 h. Intracellular HBV DNA was quantified by real-time PCR, and AST levels were measured in the co-culture supernatant.

Figure 7:
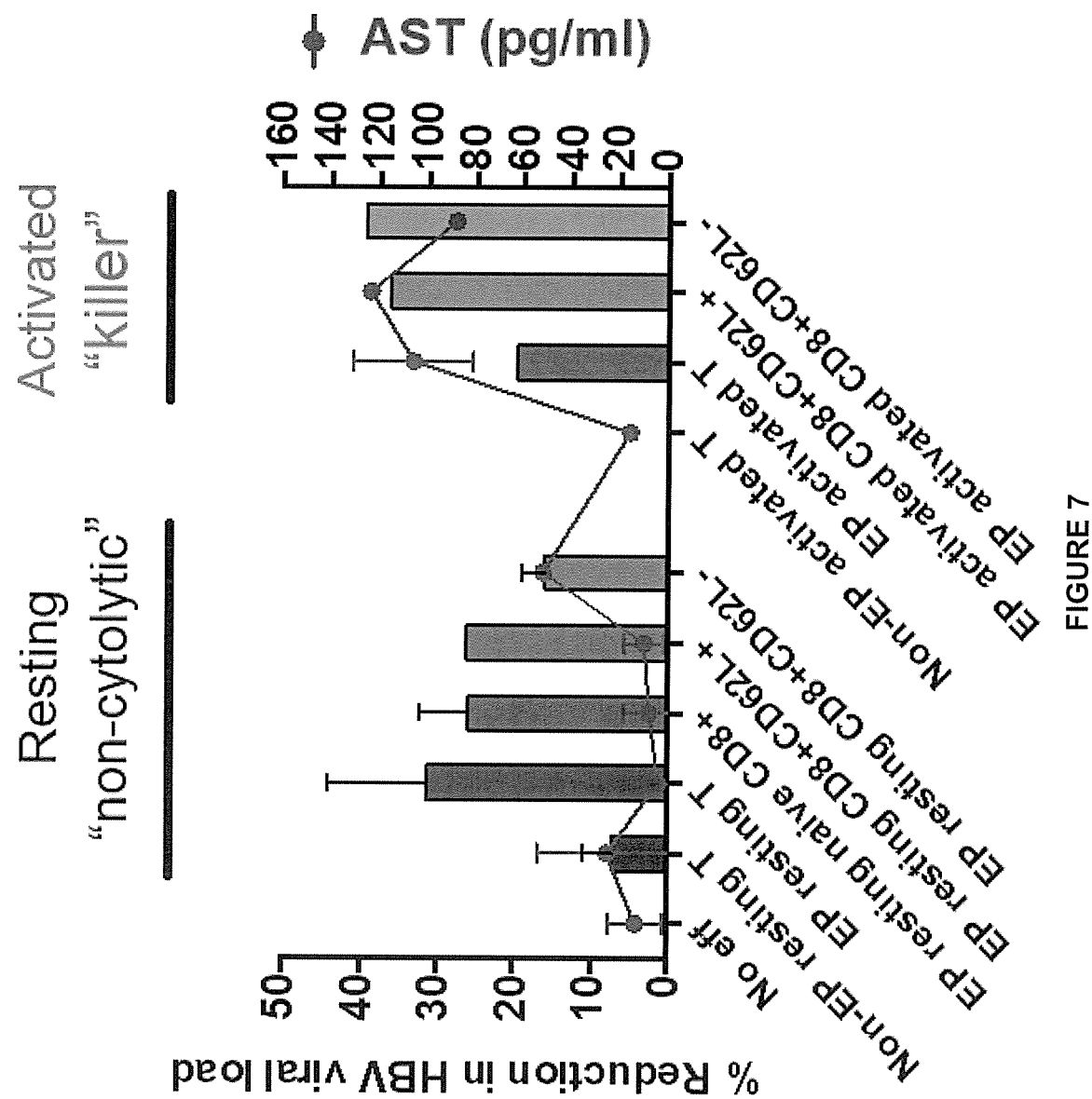
FIG. 7. Graph showing antiviral activity and cytotoxicity of T cells to HBV virus-infected liver cells at an effector: target ratio of 1:3. Bars showing inhibition of viral replication as determined by qPCR for HBV DNA, and lines showing cytolysis as determined by aspartate aminotransferase (AST) levels.
Figure 8A:
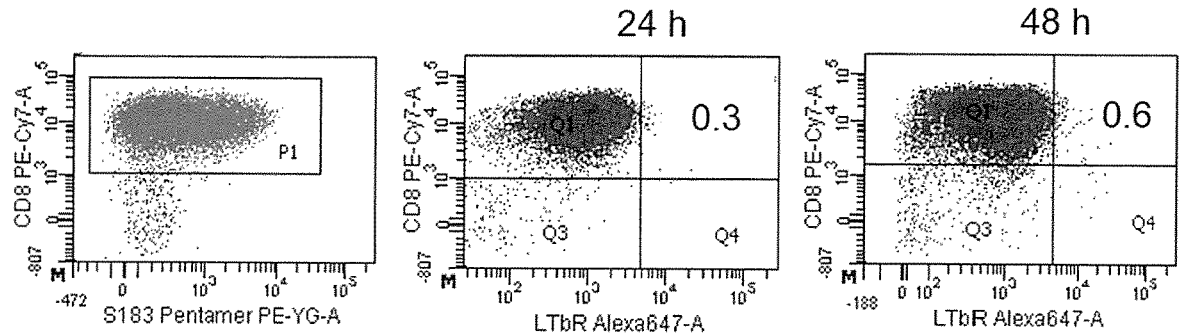
FIG. 8. Scatterplots showing expression of lymphotoxin B or LIGHT on resting CD8+ T cells. (A) Expression on HBV TCR-positive, unstimulated CD8+ T cells. (B) Expression on HBV TCR-positive, CD8+ T cells following 24 h and 48 h of stimulation with cells pulsed with TCR specific peptide. (C) Expression on HBV TCR-positive, CD8+ T cells following 24 h and 48 h of activation through CD3 and CD28. (D) Expression on HBV TCR-positive, CD8+ T cells following 24 h of treatment with IFN-γ.
Figure 8B:
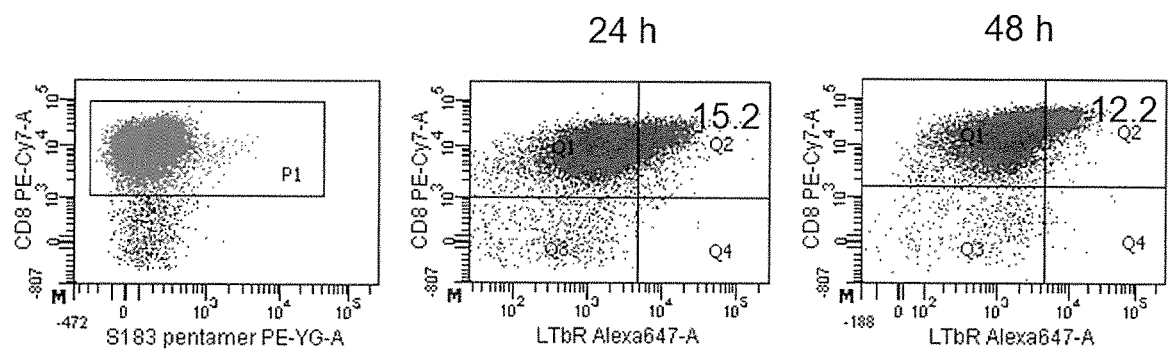
Figure 8C:
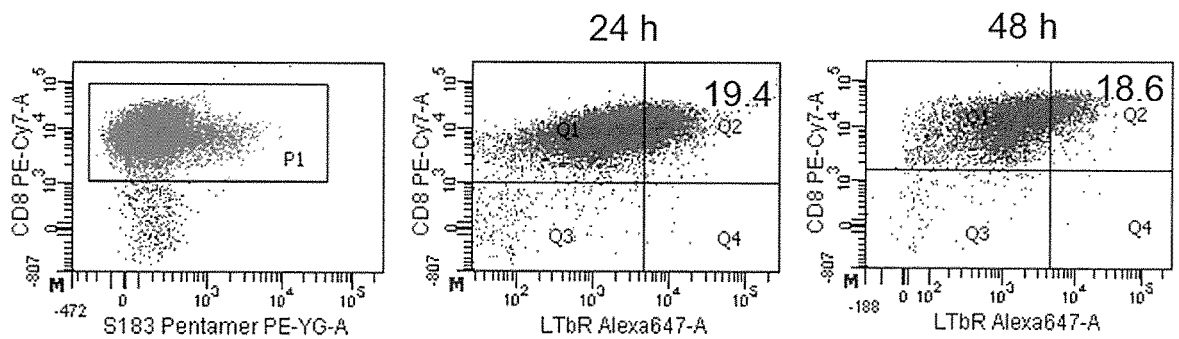
Figure 8D:
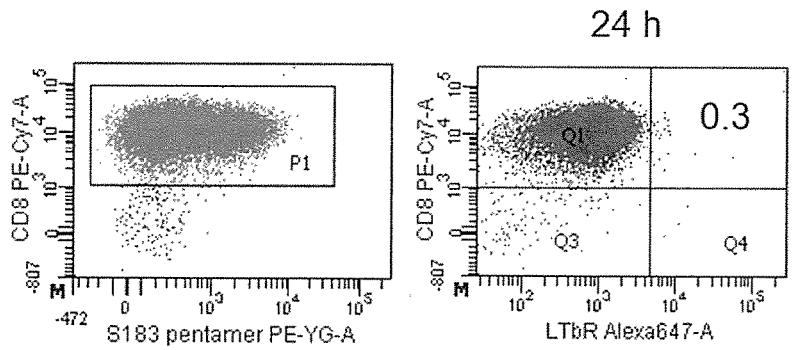

The results are shown in FIG. 7. Both electroporated, activated and electroporated, non-activated (resting) T cells were able to inhibit HBV viral load. However, electroporated, activated T cells lysed the target cells as shown by higher AST levels, whilst electroporated, non-activated T cells did not lyse the target cells.

Example 19: Investigation of the Mechanism of Antiviral Activity of HBV TCR mRNA Electroporated T Cells Recent studies have suggested that lymphotoxin-β receptor (LTβR) activation on hepatocytes can lead to degradation of HBV nuclear covalently closed circular DNA (cccDNA) without hepatotoxicity (Lucifora et al., Science (2014) 343 (6176): 1221-1228; Haybaeck et al., Cancer Cell (2009) 16(4): 295-308).

The ligands for LTβR are LTβ and LIGHT, and they are expressed on the non-activated (resting) electroporated T cells.

The invention claimed is:

1. An isolated T cell comprising an exogenous nucleic acid encoding a T Cell Receptor (TCR) specific for a hepatitis virus, wherein the T cell is a non-activated T cell and wherein the non-activated T cell has a CD45RA$^{high}$ phenotype, which is capable of inhibiting replication of the virus in a cell infected with the virus, wherein the T cell exhibits a reduced level of expression or activity of one or more cytotoxic factors as compared to the level of expression or activity of an activated T cell which is not modified for reduced expression or activity of a cytotoxic factor, and wherein the T-cell displays reduced cytotoxicity against the cells infected with, or comprising a peptide of, the virus as compared to an activated T cell comprising the TCR specific for the virus which is not modified for reduced expression or activity of a cytotoxic factor.

2. The T cell according to claim 1, wherein the non-activated T cell does not display increased expression of perforin or granzyme in response to stimulation with peptide for which the TCR is specific.

3. The T cell according to claim 1, wherein the hepatitis virus is hepatitis B virus.

4. An in vitro method for producing a modified T cell specific for a hepatitis virus, the method comprising modifying a T cell to express or comprise a T Cell Receptor (TCR) specific for the virus, wherein modifying the T cell to express or comprise the TCR specific for the virus comprises introducing a nucleic acid encoding the TCR specific for the virus into the T cell, and wherein the modified T cell is a non-activated T cell having a CD45RA$^{high}$ phenotype, which is capable of inhibiting replication of the virus in a cell infected with the virus, and wherein the method comprises modifying a T cell to reduce expression or activity of one or more cytotoxic factors, and wherein the T cell displays reduced cytotoxicity against the cells infected with, or comprising a peptide of the virus as compared to an activated T cell comprising a TCR specific for the virus which is not modified for reduced expression or activity of a cytotoxic factor.

5. The method according to claim 4, wherein the nucleic acid is introduced into the T cell by a transduction, a transfection a transposon-based system, a retroviral transduction, or a mRNA electroporation.

6. The method according to claim 4, wherein the modified, non-activated T cell does not display increased expression of perforin or granzyme in response to stimulation with peptide for which the TCR is specific.

7. The method according to claim 4, wherein the modified T cell displays reduced cytotoxicity against cells infected with, or comprising a peptide of, the virus as compared to an activated T cell comprising the TCR specific for the virus which is not modified for reduced expression or activity of the cytotoxic factor.

8. The T cell according to claim 4, wherein the hepatitis virus is hepatitis B virus.

9. An isolated T cell, wherein the T cell is obtained or obtainable by the method according to claim 4.

10. A pharmaceutical composition comprising a T cell according to claim 1 and a pharmaceutically acceptable carrier, adjuvant, excipient, or diluent.

11. The T cell according to claim 1 for use in a method of treating or preventing a disease or disorder which is caused or exacerbated by hepatitis virus infection.

12. A method of treating or preventing a disease or disorder which is caused or exacerbated by hepatitis virus infection, comprising administering to a subject a therapeutically or prophylactically effective amount of the T cell according to claim 1.

13. A method of treating or preventing a disease or disorder in a subject, comprising:
  (a) isolating at least one T cell from a subject;
  (b) modifying the at least one T cell to express or comprise a T Cell Receptor (TCR) specific for a virus wherein modifying the T cell to express or comprise the TCR specific for the virus comprises includes introducing a nucleic acid encoding the TCR specific for the virus into the at least one T cell; and
  (c) administering the modified at least one T cell to the subject;
  wherein the modified at least one T cell is a non-activated T cell having a CD45RA$^{high}$ phenotype, which is capable of inhibiting replication of the virus in a cell infected with the virus, wherein the T cell exhibits a reduced level of expression or activity of one or more cytotoxic factors as compared to the level of expression or activity of an activated T cell which is not modified for reduced expression or activity of a cytotoxic factor, and wherein the T cell displays reduced cytotoxicity against the cells infected with, or comprising a peptide of, the virus as compared to an activated T cell comprising the TCR specific for the virus which is not modified for reduced expression or activity of a cytotoxic factor.

14. The method according to claim 13, wherein the nucleic acid is introduced into the at least one T cell by transduction, transfection or transposon-based system.

15. The method according to claim 13, wherein the hepatitis virus is hepatitis B virus.

16. The method according to claim 11, wherein the disease or disorder which is caused or exacerbated by hepatitis virus infection is selected from acute hepatitis, fulminant hepatic failure, chronic hepatitis, cirrhosis, liver cancer, hepatocellular carcinoma (HCC) and pancreatic cancer.

17. The method according to claim 11, wherein the disease or disorder which is caused or exacerbated by hepatitis B virus infection.

18. A kit of parts comprising a predetermined quantity of the T cell according to claim 1.

19. The T cell according to claim 1, wherein the cytotoxic factor is selected from a group consisting of perforin, granyme B, granzyme A, granulysin, FASL, and any combination thereof.

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Hepatitis B virus

<400> SEQUENCE: 1

Phe Leu Gly Pro Leu Leu Val Leu Gln Ala
1               5                   10

<210> SEQ ID NO 2
<211> LENGTH: 10
<212> TYPE: PRT
```

```
<213> ORGANISM: Hepatitis B virus

<400> SEQUENCE: 2

Leu Leu Gly Pro Leu Leu Val Leu Gln Ala
1               5                   10

<210> SEQ ID NO 3
<211> LENGTH: 4
<212> TYPE: PRT
<213> ORGANISM: Picornavirus

<400> SEQUENCE: 3

Asn Pro Gly Pro
1
```